(12) United States Patent
Gillespie, III et al.

(10) Patent No.: US 7,988,675 B2
(45) Date of Patent: Aug. 2, 2011

(54) AUTOMATIC INJECTION AND RETRACTION DEVICES FOR USE WITH PRE-FILLED SYRINGE CARTRIDGES

(75) Inventors: Richard D. Gillespie, III, Athens, TX (US); Doug Owen Crow, Ben Wheeler, TX (US)

(73) Assignee: West Pharmaceutical Services of Delaware, Inc., Wilmington, DE (US)

( * ) Notice: Subject to any disclaimer, the term of this patent is extended or adjusted under 35 U.S.C. 154(b) by 1097 days.

(21) Appl. No.: 11/669,452

(22) Filed: Jan. 31, 2007

(65) Prior Publication Data

US 2007/0135767 A1   Jun. 14, 2007

Related U.S. Application Data

(63) Continuation-in-part of application No. 11/296,973, filed on Dec. 8, 2005, now Pat. No. 7,674,246.

(51) Int. Cl.
*A61M 5/00*   (2006.01)
(52) U.S. Cl. .................................................. 604/181
(58) Field of Classification Search .............. 604/192, 604/195, 197, 198, 187, 110, 263, 162, 218, 604/171, 181
See application file for complete search history.

(56) References Cited

U.S. PATENT DOCUMENTS

| | | | |
|---|---|---|---|
| 2,561,233 A | 7/1951 | Ryan et al. |
| 3,306,290 A | 2/1967 | Weltman |
| 3,572,336 A | 3/1971 | Hershberg |
| 3,705,582 A | 12/1972 | Stumpf et al. |
| 3,707,968 A | 1/1973 | Koenig |
| 3,708,089 A | 1/1973 | Holder et al. |
| 3,834,387 A | 9/1974 | Brown |
| 3,901,402 A | 8/1975 | Ayres |
| 4,059,109 A | 11/1977 | Tischlinger |
| 4,445,895 A | 5/1984 | Margulies |
| 4,542,749 A | 9/1985 | Caselgrandi et al. |

(Continued)

FOREIGN PATENT DOCUMENTS

CN   1011761 A   6/1987

(Continued)

OTHER PUBLICATIONS

Office Action Issued Apr. 17, 2009 in related U.S. Appl. No. 11/296,973.

(Continued)

*Primary Examiner* — Manuel A Mendez
(74) *Attorney, Agent, or Firm* — Panitch Schwarze Belisario & Nadel LLP

(57) ABSTRACT

An automatic injection and retraction device having a longitudinal axis is provided that includes an injection assembly, a retraction assembly, and a pre-filled syringe cartridge. The injection assembly has an activation-prevention feature moveable between an on position and an off position. The retraction assembly has a needle guard that is removable in a direction along the longitudinal axis upon application of a removal force. The pre-filled syringe cartridge has a hypodermic needle with a needle sheath thereon. The retraction and injection assemblies are secured to one another so that the pre-filled syringe cartridge is in the retraction assembly with the needle sheath secured to the needle guard. The retraction and injection assemblies are configured so that, upon application of a twisting torque to the injection and retraction assemblies, the activation-prevention feature moves from the on position to the off position simultaneous with applying the removal force to the needle guard.

20 Claims, 19 Drawing Sheets

U.S. PATENT DOCUMENTS

| | | |
|---|---|---|
| 4,581,016 A | 4/1986 | Gettig |
| D286,164 S | 10/1986 | Tinz |
| D287,603 S | 1/1987 | Bruhn |
| 4,643,721 A | 2/1987 | Brunet |
| 4,689,042 A | 8/1987 | Sarnoff et al. |
| 4,755,169 A | 7/1988 | Sarnoff et al. |
| 4,767,413 A | 8/1988 | Haber et al. |
| 4,795,444 A | 1/1989 | Hasegawa et al. |
| 4,820,286 A | 4/1989 | van der Wal |
| 4,822,340 A | 4/1989 | Kamstra |
| 4,861,335 A | 8/1989 | Reynolds |
| 4,886,495 A | 12/1989 | Reynolds |
| 4,898,580 A | 2/1990 | Crowley |
| 4,969,877 A | 11/1990 | Kornberg |
| 4,998,922 A | 3/1991 | Kuracina et al. |
| 5,045,058 A | 9/1991 | Demetrakopoulos |
| 5,049,133 A | 9/1991 | Villen Pascual |
| 5,085,641 A | 2/1992 | Sarnoff et al. |
| 5,085,642 A | 2/1992 | Sarnoff et al. |
| 5,092,843 A | 3/1992 | Monroe et al. |
| 5,102,393 A | 4/1992 | Sarnoff et al. |
| 5,120,310 A | 6/1992 | Shaw |
| 5,137,511 A | 8/1992 | Reynolds |
| 5,169,385 A | 12/1992 | Turnbull |
| 5,176,657 A | 1/1993 | Shields |
| 5,188,613 A | 2/1993 | Shaw |
| D339,606 S | 9/1993 | Podobrin |
| 5,267,961 A | 12/1993 | Shaw |
| 5,295,965 A | 3/1994 | Wilmot |
| 5,300,030 A | 4/1994 | Crossman et al. |
| 5,324,273 A | 6/1994 | Discko, Jr. |
| 5,358,489 A | 10/1994 | Wyrick |
| 5,364,363 A | 11/1994 | Pearson et al. |
| 5,383,865 A | 1/1995 | Michel |
| 5,385,551 A | 1/1995 | Shaw |
| 5,389,076 A | 2/1995 | Shaw |
| 5,391,151 A | 2/1995 | Wilmot |
| 5,411,487 A | 5/1995 | Castagna |
| 5,411,489 A | 5/1995 | Pagay et al. |
| 5,413,564 A | 5/1995 | Silver et al. |
| 5,423,758 A | 6/1995 | Shaw |
| 5,425,715 A | 6/1995 | Dalling et al. |
| 5,466,223 A | 11/1995 | Bressler et al. |
| 5,531,255 A | 7/1996 | Vacca |
| 5,540,664 A | 7/1996 | Wyrick |
| 5,545,145 A | 8/1996 | Clinton et al. |
| 5,578,011 A | 11/1996 | Shaw |
| 5,599,309 A | 2/1997 | Marshall et al. |
| 5,620,421 A | 4/1997 | Schmitz |
| 5,632,733 A | 5/1997 | Shaw |
| 5,637,092 A | 6/1997 | Shaw |
| 5,643,214 A | 7/1997 | Marshall et al. |
| 5,665,071 A | 9/1997 | Wyrick |
| 5,674,204 A | 10/1997 | Chanoch |
| 5,685,846 A | 11/1997 | Michaels, Jr. |
| 5,688,251 A | 11/1997 | Chanoch |
| 5,695,472 A | 12/1997 | Wyrick |
| 5,779,677 A | 7/1998 | Frezza |
| 5,779,679 A | 7/1998 | Shaw |
| 5,810,775 A | 9/1998 | Shaw |
| 5,817,058 A | 10/1998 | Shaw |
| RE35,986 E | 12/1998 | Ritson et al. |
| 5,860,961 A | 1/1999 | Gettig |
| 5,873,462 A | 2/1999 | Nguyen et al. |
| 5,921,966 A | 7/1999 | Bendek et al. |
| 5,931,817 A | 8/1999 | Nguyen et al. |
| 5,941,857 A | 8/1999 | Nguyen et al. |
| 5,944,700 A | 8/1999 | Nguyen et al. |
| D414,201 S | 9/1999 | Larson et al. |
| 5,957,896 A | 9/1999 | Bendek et al. |
| 5,957,897 A | 9/1999 | Jeffrey |
| D414,807 S | 10/1999 | Baudino et al. |
| 5,961,495 A | 10/1999 | Walters et al. |
| 5,989,220 A | 11/1999 | Shaw et al. |
| 5,997,512 A | 12/1999 | Shaw |
| 6,001,082 A | 12/1999 | Dair et al. |
| 6,015,438 A | 1/2000 | Shaw |
| D423,577 S | 4/2000 | Baudino et al. |
| D425,120 S | 5/2000 | Ramil |
| 6,086,563 A | 7/2000 | Moulton et al. |
| 6,095,814 A | 8/2000 | Petrich et al. |
| 6,099,503 A | 8/2000 | Stradella |
| 6,149,623 A | 11/2000 | Reynolds |
| 6,183,445 B1* | 2/2001 | Lund et al. .............. 604/198 |
| 6,200,627 B1 | 3/2001 | Lubrecht |
| 6,210,315 B1 | 4/2001 | Andrews et al. |
| 6,210,369 B1 | 4/2001 | Wilmot et al. |
| 6,210,371 B1 | 4/2001 | Shaw |
| 6,213,597 B1 | 4/2001 | Liu |
| 6,221,046 B1 | 4/2001 | Burroughs et al. |
| 6,221,053 B1 | 4/2001 | Walters et al. |
| 6,221,055 B1 | 4/2001 | Shaw et al. |
| D441,398 S | 5/2001 | Owen et al. |
| 6,248,095 B1 | 6/2001 | Giambattista et al. |
| D446,242 S | 8/2001 | Stukenkemper |
| 6,277,099 B1 | 8/2001 | Strowe et al. |
| D452,271 S | 12/2001 | Owen et al. |
| 6,328,715 B1 | 12/2001 | Dragan et al. |
| 6,346,094 B2 | 2/2002 | West et al. |
| 6,349,850 B1 | 2/2002 | Cheikh |
| 6,387,078 B1 | 5/2002 | Gillespie, III |
| 6,494,863 B1 | 12/2002 | Shaw et al. |
| 6,572,584 B1 | 6/2003 | Shaw et al. |
| 6,638,244 B1 | 10/2003 | Reynolds |
| 6,689,118 B2 | 2/2004 | Alchas et al. |
| 6,793,646 B1 | 9/2004 | Giambattista et al. |
| 6,796,967 B2 | 9/2004 | Jensen |
| 6,802,828 B2 | 10/2004 | Reynolds |
| 2001/0002434 A1 | 5/2001 | Lubrecht |
| 2001/0029354 A1 | 10/2001 | Rolle et al. |
| 2001/0039400 A1 | 11/2001 | Lubrecht |
| 2002/0010430 A1 | 1/2002 | Dragan et al. |
| 2002/0164265 A1 | 11/2002 | Hetzler |
| 2002/0177819 A1 | 11/2002 | Barker et al. |
| 2003/0083621 A1 | 5/2003 | Shaw et al. |
| 2003/0088216 A1 | 5/2003 | Py |
| 2003/0100866 A1 | 5/2003 | Reynolds |
| 2003/0130626 A1 | 7/2003 | VanTassel et al. |
| 2003/0187388 A1 | 10/2003 | Sharon et al. |
| 2004/0024367 A1 | 2/2004 | Gilbert |
| 2004/0111064 A1* | 6/2004 | Asbaghi .................. 604/198 |
| 2005/0049551 A1* | 3/2005 | Kirchhofer .............. 604/82 |
| 2005/0113763 A1 | 5/2005 | Reynolds |
| 2006/0178629 A1 | 8/2006 | Gillespie et al. |
| 2006/0178631 A1* | 8/2006 | Gillespie et al. .......... 604/139 |

FOREIGN PATENT DOCUMENTS

| | | |
|---|---|---|
| JP | 10057483 A | 3/1998 |
| WO | 9535126 A1 | 12/1995 |
| WO | 2006063124 A2 | 6/2006 |

OTHER PUBLICATIONS

Office Action Issued Mar. 29, 2006 in related U.S. Appl. No. 11/297,159.
Office Action Issued Apr. 11, 2007 in related U.S. Appl. No. 11/297,159.
Office Action Issued Dec. 31, 2007 in related U.S. Appl. No. 11/297,159.
Office Action Issued Nov. 13, 2008 in related U.S. Appl. No. 11/297,159.
Office Action Issued 11/1/06 in related U.S. Appl. No. 11/297,225.
Office Action Issued Jun. 30, 2009 in related U.S. Appl. No. 11/297,225.
Office Action Issued Nov. 25, 2009 in related U.S. Appl. No. 11/297,225.
International Preliminary report on Patentability in related International Application PCT/US05/44410; dated Jan. 17, 2007.
Examination Report and Written Opinion Issued Jun. 27, 2008 in related Singapore Application No. 200704199-9.
Examination Report dated Jul. 7, 2009 in related Singapore Application No. 200704201-3.
Chinese Office Action for the related Chinese Application No. 200680026185.7 dated Mar. 1, 2010.
Office Action for the related U.S. Appl. No. 11/458,114 dated Apr. 28, 2010.

International Search Report for the corresponding International Patent Application No. PCT/US08/52427; mailed Aug. 4, 2008; 3 pages.
International Preliminary Report on Patentability for related International Application No. PCT/US05/44411, mailed Oct. 6, 2008.
International Search Report and Written Opinion for related International Application No. PCT/US05/44411, mailed Jun. 21, 2007.
International Search Report for related International Application No. PCT/US05/44492 and written opinion; dated May 25, 2006.
International Search Report and Written Opinion for related International Application No. PCT/US08/52427; dated Aug. 4, 2008.
International Search Report and Written Opinion for related International Application No. PCT/US05/44410; dated Jun. 27, 2006.
International Search Report for related International Application No. PCT/US06/27733, dated Apr. 23, 2007.
Office Action for related Chinese Patent Application No. 200580047001.0 issued Jul. 17, 2009.
First Office Action for related Chinese Patent Application No. 200580047294.2; mailed Aug. 21, 2009; 7 pages (English translation only).
Supplementary Search Report for the related European Application No. 05853353.0 dated Apr. 23, 2010.
Chinese Office Action dated May 25, 2010 in related Chinese Application No. 200580046736.1.
Office Action issued Oct. 6, 2010 in U.S. Appl. No. 11/458,114.

* cited by examiner

AUTOMATIC INJECTION AND RETRACTION DEVICES FOR USE WITH PRE-FILLED SYRINGE CARTRIDGES

CROSS REFERENCE TO RELATED APPLICATIONS

This application is a continuation-in-part of U.S. application Ser. No. 11/296,973 filed Dec. 8, 2005, now U.S. Pat. No. 7,674,246, issued Mar. 9, 2010, the entire contents of which are incorporated herein by reference.

BACKGROUND OF THE INVENTION

1. Field of the Invention

The present disclosure is related to automatic injection and retraction devices. More particularly, the present disclosure is related to automatic injection and retraction devices for use with pre-filled syringe cartridges.

2. Description of Related Art

Manually activated pre-filled syringe cartridges are commercially available from a variety of manufacturers. One such example is the HYPAK® syringe, manufactured by Becton Dickinson & Company. Pre-filled syringe cartridges are used in the administration of drug solutions, drug suspensions, antidotes, dietary supplements, and any other liquid medicament (hereinafter collectively referred to as "liquid medicament") by parenteral injection.

As such, pre-filled syringe cartridges include a medicine compartment, a hypodermic needle permanently affixed to and in fluid communication with the medicine compartment, and a piston slidably received in the medicine compartment. Often times, the pre-filled syringe cartridges include a plunger removably secured to the piston for causing the piston to force the liquid medicament from the needle. Pre-filled syringes are typically prepared by pharmaceutical companies or sterile filling contractors in a sterile filling suite in which the liquid medicament and the syringe are brought together in a sterile manufacturing environment wherein all components and drug solutions are isolated from microbial contamination. Pre-filled syringe cartridges also include a needle sheath removably positioned over the needle, wherein the sheath is removed just prior to use. The needle sheath serves to protect the needle from physical damage and maintains the fluid path in a sterile condition until it is removed prior to use.

Blood borne diseases such as AIDS, Hepatitis C, and others, are increasing within the general population. The onset of these diseases has increased the desire to prevent inadvertent needle sticks during the use of injection apparatus, including pre-filled syringe cartridges. In order to mitigate inadvertent needle sticks, many pre-filled syringe cartridges include a safety guard that covers the needle once withdrawn from the patient.

In contrast to manually activated pre-filled syringe cartridges, automatic injection devices, commonly known as "auto-injectors", are also available. Such auto-injectors, once triggered by the user, use an automatic mechanism to insert a hypodermic needle into the recipient's flesh at the injection site and force the liquid medicament out of a medicine compartment, through the hypodermic needle, and into the recipient. In addition to automatic needle insertion and dose delivery, some auto-injectors also incorporate retraction mechanisms to automatically retract the needle after use. Auto-injectors have proven particularly useful in allowing the medically untrained user to administer a parenteral injection. Auto-injectors help to guise the injection apparatus, which benefits patients exhibiting psychological paranoia (i.e., "needle phobic" individuals and young children). Patients with limited manual dexterity or other physical constraints that may prevent the use of conventional syringes (or pre-filled syringe cartridges) can attain self-reliance in injection therapy through the use of auto-injector technology.

Some auto-injectors have been designed to accept commercially available, manually activated pre-filled syringe cartridges. Unfortunately, such auto-injectors have proven difficult to load with the pre-filled syringe cartridges, have proven ineffective at maintaining the auto-injector in a cocked position, have proven ineffective at maintaining the sterility of the needle, and/or have been too difficult to activate. In order to maintain the sterility of the needle, some prior art auto-injectors are configured to drive the needle through the needle sheath during use, which has been found to increase patient discomfort and increase a risk of "coring" the elastomeric needle sheath.

Accordingly, there is a need for automatic injection and retraction devices that overcome, alleviate, and/or mitigate one or more of the aforementioned and other deleterious effects of the prior art.

BRIEF SUMMARY OF THE INVENTION

Automatic injection and retraction devices are provided that facilitate the on-board storage and use of commercially available pre-filled syringe cartridges.

Automatic injection and retraction devices are also provided that are configured for use with commercially available pre-filled syringe cartridges without the need for initially removing the needle sheath from the cartridge, but which easily removes the needle sheath at the time of use. In some embodiments, the automatic injection and retraction device is configured to make use of a shoulder present on many commercially available pre-filled syringe cartridges to assist in removing the needle sheath at the time of use.

Further, automatic injection and retraction devices are provided that are configured so that, at the time of use, the same manual movement that disables the activation-prevention feature of the auto-injector concurrently removes the needle sheath from the pre-filled syringe cartridge.

In some embodiments, automatic injection and retraction devices are provided that permanently disable the activation-prevention feature of the auto-injector when the device is prepared for use.

In other embodiments, automatic injection and retraction devices are provided that disable the activation-prevention feature and remove the needle sheath by rotational movement.

Still further, automatic injection and retraction devices are provided that are configured so that, after use, the needle can be safely and permanently re-capped with a sheath and protective cover, thereby containing the used hypodermic needle within the auto-injector, and thereby rendering the used auto-injector safe for disposal as conventional solid waste.

An automatic injection and retraction device having a longitudinal axis is provided. In some embodiments, the device includes an injection assembly, a retraction assembly, and a pre-filled syringe cartridge. The injection assembly has an activation-prevention feature moveable between an on position and an off position. The retraction assembly has a needle guard that is removable from the retraction assembly in a direction along the longitudinal axis upon application of a removal force. The pre-filled syringe cartridge has a hypodermic needle with a needle sheath thereon. The retraction and injection assemblies are secured to one another so that the pre-filled syringe cartridge is disposed in the retraction assembly with the needle sheath secured to the needle guard. The retraction and injection assemblies are configured so that, upon application of a twisting torque to the injection and retraction assemblies about the longitudinal axis, the activation-prevention feature moves from the on position to the off position simultaneous with applying the removal force to the needle guard.

In other embodiments, automatic injection and retraction device having a longitudinal axis is provided that includes an injection assembly, a retraction assembly, and a pre-filled syringe cartridge. The injection assembly has an activation sub-assembly and an injection sub-assembly. The activation sub-assembly is rotatable with respect the injection sub-assembly about the longitudinal axis but not moveable with respect to the injection sub-assembly along the longitudinal axis. The retraction assembly has a retraction sub-assembly and a needle guard. The needle guard is moveable with respect the retraction sub-assembly along the longitudinal axis but not rotatable with respect to the retraction sub-assembly along the longitudinal axis. The pre-filled syringe cartridge has a hypodermic needle with a needle sheath thereon. The retraction assembly is secured to the injection assembly so that the pre-filled syringe cartridge is disposed in the retraction assembly with the needle sheath secured to the needle guard. The needle guard having the needle sheath secured thereto is removed from the retraction sub-assembly in a direction along the longitudinal axis upon application of a twisting torque to the activation sub-assembly and the needle guard about the longitudinal axis.

A method of providing a parenteral injection of liquid medicament is also provided. The method includes twisting an injection assembly with respect to a retraction assembly so that the injection assembly is simultaneously moved to an armed position and the retraction assembly is separated from a needle guard, where the needle guard is engaged to a needle sheath so that separation of the needle guard from the retraction assembly removes the needle sheath from a hypodermic needle within the retraction assembly.

The above-described and other features and advantages of the present disclosure will be appreciated and understood by those skilled in the art from the following detailed description, drawings, and appended claims.

DETAILED DESCRIPTION OF THE INVENTION

Figure 1:
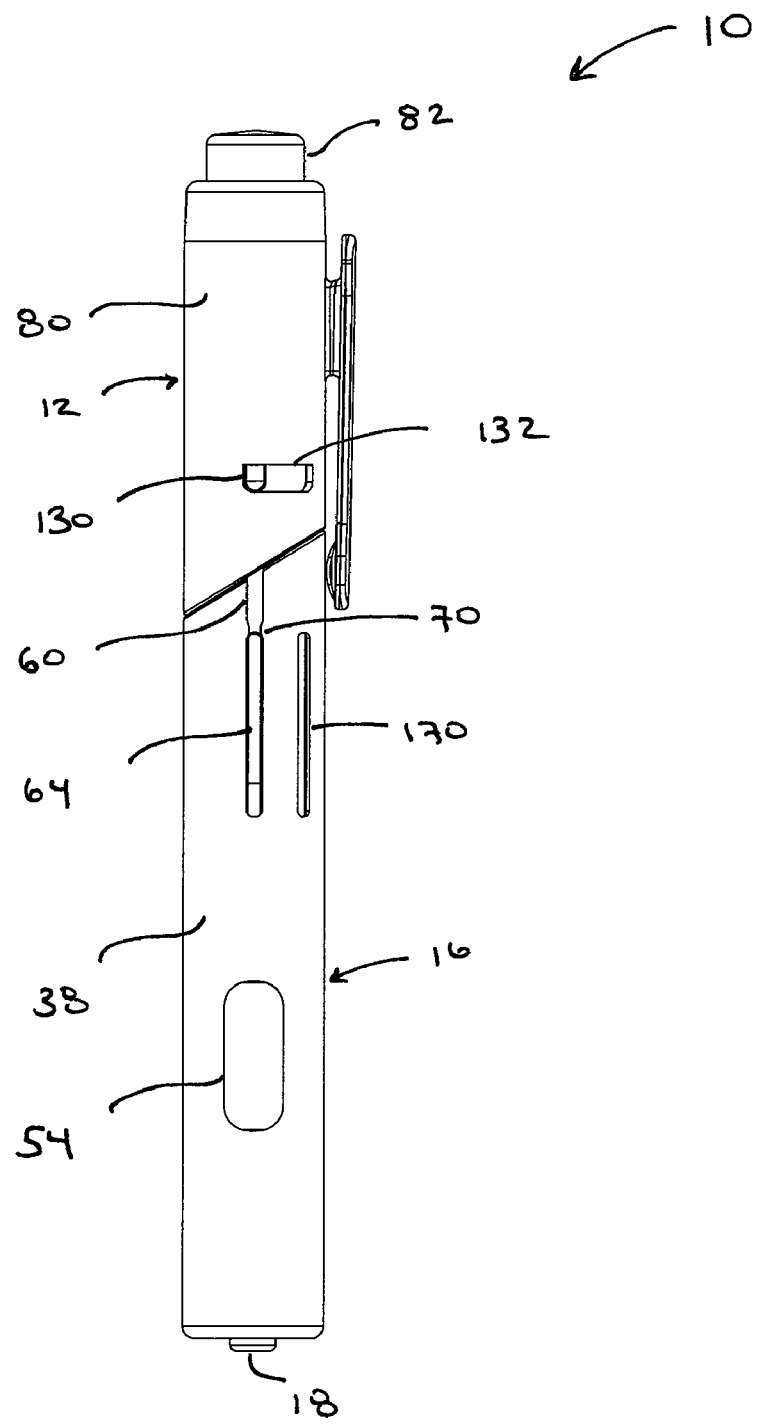
FIG. 1 is a first side view of an exemplary embodiment of an automatic injection and retraction device according to the present disclosure.

Referring to the drawings and in particular to FIGS. 1 through 4, an exemplary embodiment of an automatic injection and retraction device 10 (hereinafter "auto-injector") according to the present invention is shown. Auto-injector 10 includes an injection assembly 12, a pre-filled syringe cartridge 14, and a guarded retraction assembly 16.

Advantageously, auto-injector 10 is configured for use with commercially available pre-filled syringe cartridges 14 without the need for removing a needle sheath 18 from the cartridge during assembly of the pre-filled syringe cartridge into the auto-injector. In this manner, the hypodermic needle 20 of pre-filled syringe cartridge 14 retains the sterile condition as provided by the manufacturer. Rather, auto-injector 10 is configured so that, at the time of use, the same manual movement that "arms" auto-injector 10 also removes needle sheath 18.

Figure 4:
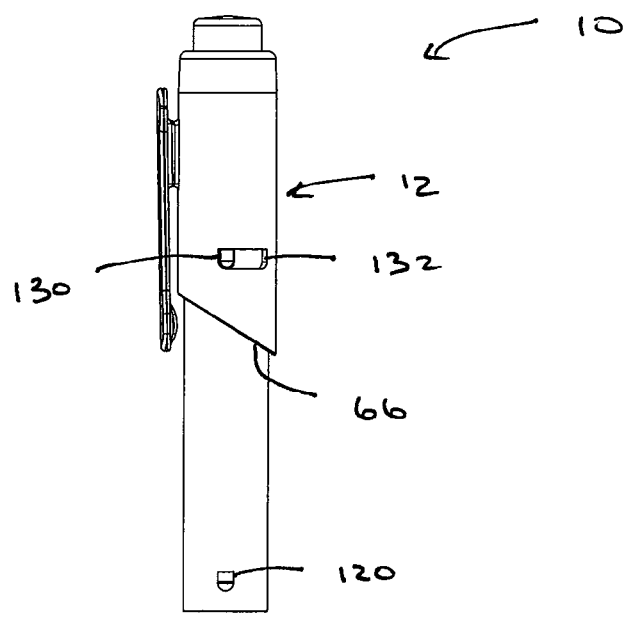
FIG. 4 is a partially exploded view of FIG. 3, illustrating the automatic injection and retraction device as shipped from the factory.
Figure 4:
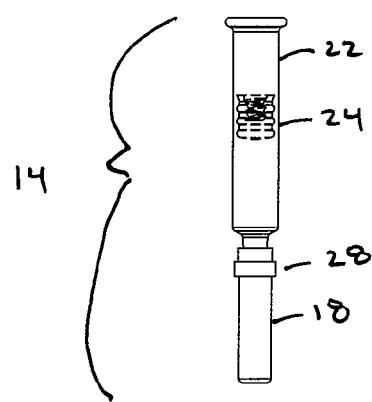
Figure 4:
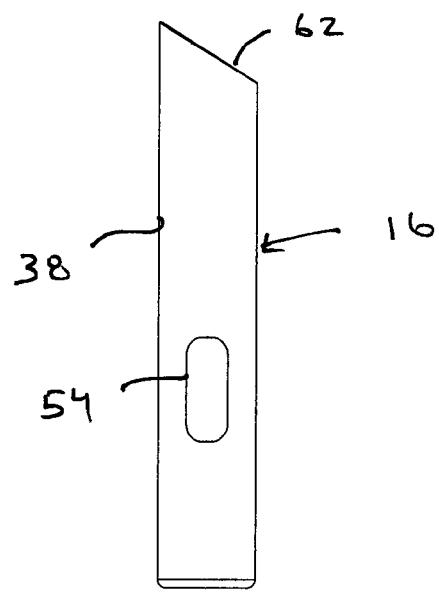

Referring to FIG. 4, auto-injector 10 accepts the commercially available pre-filled syringe cartridge 14 unaltered from the condition the cartridge was shipped from the factory. More particularly, auto-injector 10 accepts pre-filled syringe cartridge 14 together with needle sheath 18. Auto-injector 10 also provides for an easy and straightforward method for removing needle sheath 18 at the same time that the auto-injector is armed for use.

Once activated, injection assembly 12 is configured to move pre-filled syringe cartridge 14 so that hypodermic needle 20 extends from retraction assembly 16 into a user and to inject the single, pre-measured dose of medicament from the cartridge into the user. Once the injection is complete, injection assembly 12 is disabled so that retraction assembly 16 automatically retracts hypodermic needle 20.

Figure 2:
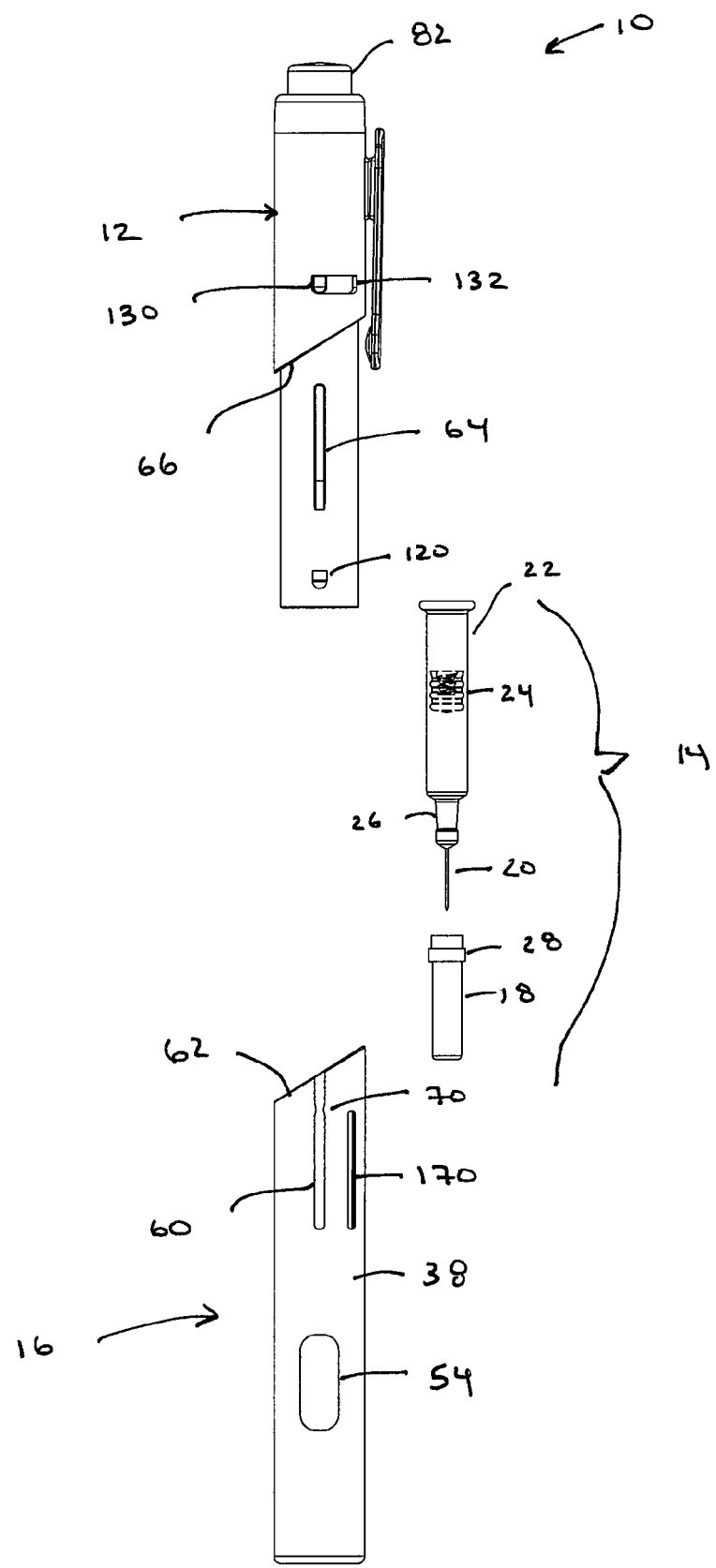
FIG. 2 is a partially exploded view of FIG. 1.
Figure 3:
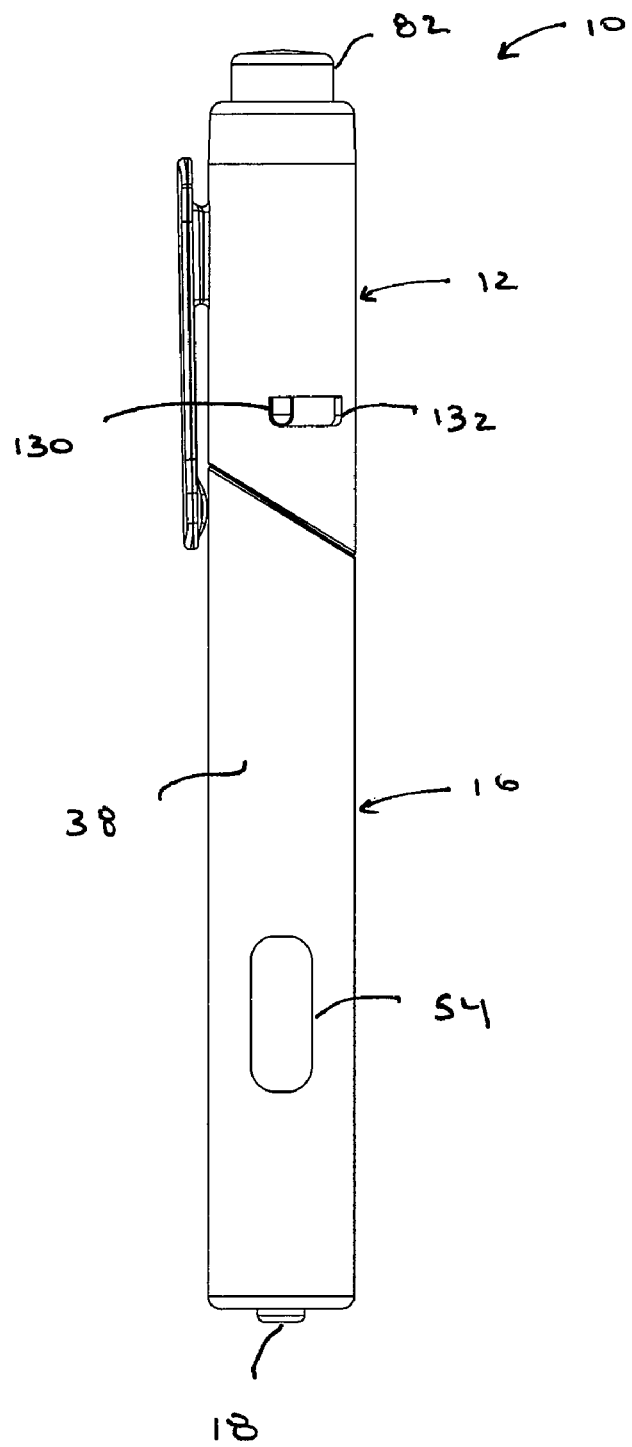
FIG. 3 is an opposite side view of the automatic injection and retraction device of FIG. 1.

Referring to FIGS. 2 and 4 and as is known by those skilled in the art, pre-filled syringe cartridges as exemplified by cartridge 14 includes a hypodermic needle 20 permanently affixed to and in fluid communication with a medicine compartment 22. Medicine compartment 22 is filled, during manufacture of cartridge 14, with a predetermined charge of liquid medicament (not shown). Cartridge 14 further includes a piston 24 (shown in phantom) slidably received in medicine compartment 22. In one exemplary embodiment, needle sheath 18 is an elastomeric member forming a removable interference fit with a portion 26 of medicine compartment 22. As is also known in the art, needle sheath 18 is configured to maintain hypodermic needle 20 in a sterile condition. In addition, needle sheath 18 has a shoulder 28 defined thereon.

For purposes of clarity, pre-filled syringe cartridge 14 is illustratively described herein by way of example as a HYPAK® syringe commercially available from Becton Dickinson & Company. Of course, it is contemplated by the present disclosure for auto-injector 10 to find use with other commercially available pre-filled syringe cartridges having needle sheath 18 with shoulder 28.

Figure 5:
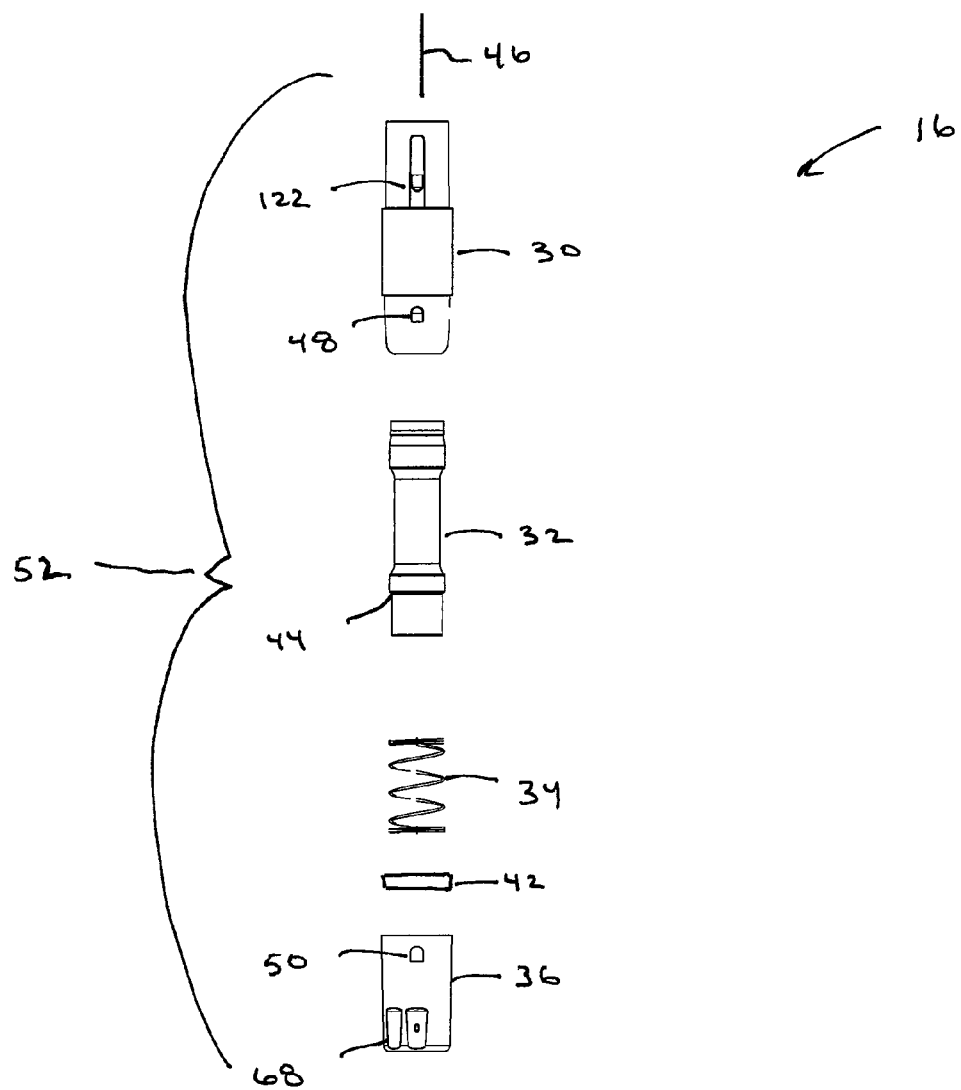
FIG. 5 is an exploded view of an exemplary embodiment of a retraction assembly according to the present disclosure.
Figure 5:
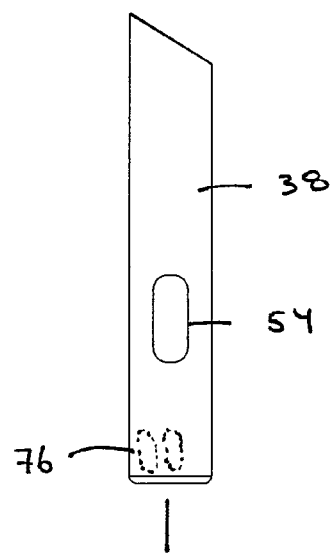

Referring to FIG. 5, retraction assembly 16 includes a window tube 30, a syringe guide 32, a return spring 34, a nose 36, and a guard 38. Advantageously, and as more particularly described in FIG. 7, guard 38 is configured to make use of shoulder 28 to assist in removing needle sheath 18 from cartridge 14 as discussed herein below.

Figure 6:
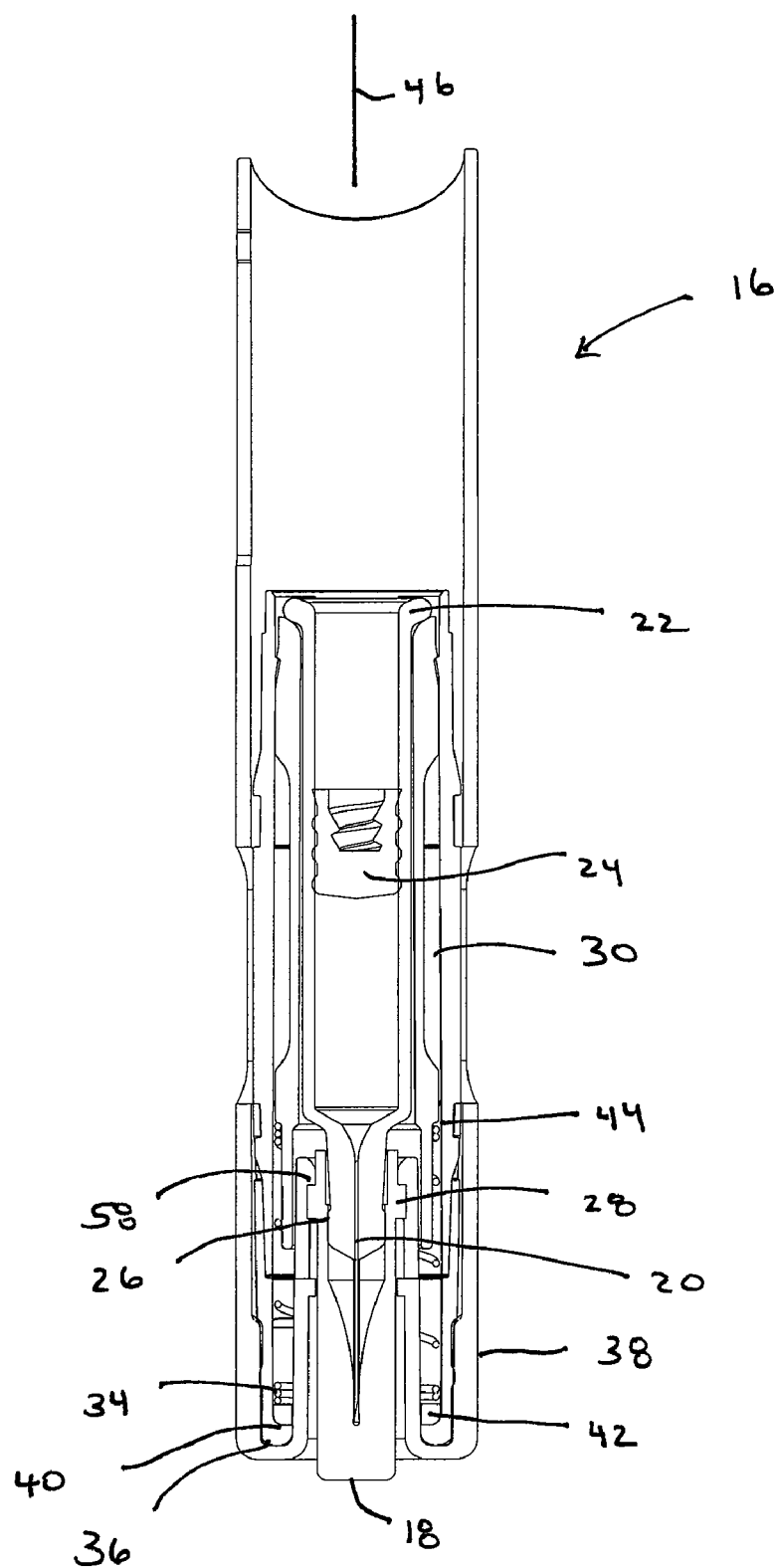
FIG. 6 is a partial cross section of the retraction assembly of FIG. 1 before the removal of the guard and the needle sheath.
Figure 7:
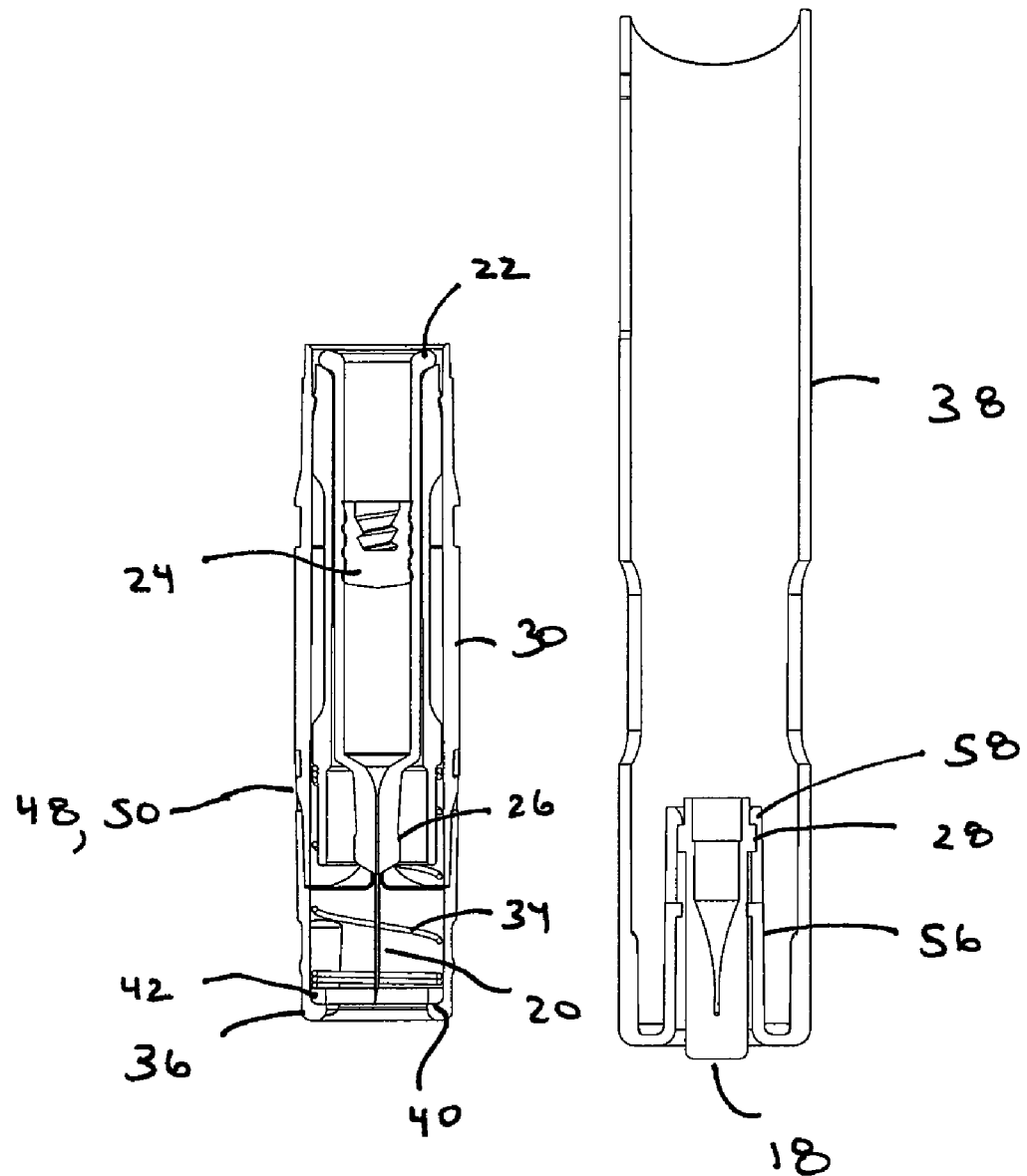
FIG. 7 is a partial cross section of the retraction assembly of FIG. 1 after the removal of the guard and the needle sheath.

Referring to FIGS. 6 and 7, upon assembly of retraction device 16, a bottom end of retraction spring 34, rests within nose 36 and is supported by a bottom support surface 40 of the nose. In some embodiments, retraction assembly 16 can include an elastomeric damper pad 42 residing between spring 34 and support surface 40. Preferably, damper pad 42 is co-molded within nose 36. The top end of retraction spring 34 is disposed over a portion of syringe guide 32 and rests on a top support surface 44 of the syringe guide. In this manner, retraction spring 34 is configured to act on syringe guide 32 for retracting syringe cartridge 14 into retraction assembly 16 as described herein below.

Referring to FIG. 7, window tube 30 is rigidly connected to nose 36 so that syringe guide 32 is movable through the tube parallel to a longitudinal axis 46 of auto-injector 10. For example, window tube 30 can include one or more tabs 48 (two shown) that mate with a corresponding number of openings 50 defined in nose 36. Thus, window tube 30 is connected to nose 36 so that the window tube and the nose can not rotate with respect to one another about axis 46. Once assembled, window tube 30, syringe guide 32, return spring 34, nose 36, and optionally, impact damper 42, form a retraction sub-assembly 52.

Similarly, retraction sub-assembly 52 is received within guard 38 so that the guard can move in relation to the retraction sub-assembly in a direction parallel to axis 46, but the guard is restrained from rotating with respect to the retraction sub-assembly about the axis 46.

The various components of retraction assembly 16 are preferably substantially transparent and/or include aligned openings to allow a user a direct line of sight to syringe cartridge 14. For example, in the illustrated embodiment, window tube 30 and syringe guide 32 are made of substantially transparent plastic material, while guard 38 includes a sight opening 54 defined therethrough. In this manner, a user can see medicine compartment 22 of cartridge 14 to verify one or more attributes of the liquid medicament before and/or after use of auto-injector 10.

Referring to FIGS. 6 and 7, guard 38 includes an inner housing member 56, configured to engage shoulder 28 of needle sheath 18. In the illustrated embodiment, inner housing member 56 includes a recess 58 defined therein. Recess 58 is configured to receive and retain shoulder 28 of sheath 18. More particularly, needle sheath 18 is sufficiently resilient so that, during installation of cartridge 14 into retraction assembly 16, the needle sheath can flex or deform until shoulder 28 is received in and retained by recess 58.

In other embodiments of the present disclosure, inner housing member 56 can be configured to resiliently flex outward, during installation of cartridge 14 into retraction assembly 16, so that until shoulder 28 is received in and retained by recess 58. In still other embodiments, both inner housing member 56 and needle sheath 18 can resiliently flex, during installation of cartridge 14 into retraction assembly 16, so that until shoulder 28 is received in and retained by recess 58.

Advantageously, the interconnection between shoulder 28 and recess 58 provides greater securement then the interconnection between needle sheath 18 and portion 26 of medicine compartment 22. Thus, the linear movement of guard 38 downward along the longitudinal axis 46 results in needle sheath 18 being retained by the guard and removed from cartridge 14 so that the sheath is removed along with guard 38. Importantly and as best seen in FIG. 7, needle 20 remains positioned internal to retraction assembly 16 even though needle sheath 18 and guard 38 have been removed.

After the installation of syringe cartridge 14 into retraction assembly 16, the retraction assembly is permanently affixed to injection assembly 12. Attachment may be accomplished by, for example, a cooperating snap-fit device. In one embodiment, window tube 30 of retraction assembly can be affixed to a portion of injection assembly 12 (i.e., inner housing 84 discussed herein below) so as to prevent relative movement between the window tube and the inner housing in any direction after final assembly. During final assembly, the permanent attachment of window tube 30 to inner housing 84 permanently captures syringe cartridge 14 therein. Once window tube 30 and inner housing 84 are assembled, a different portion of injection assembly 12 (i.e., cap 80 discussed herein below) remains free to rotate—but not translate—relative to inner housing 84, and guard 38 remains free to move in the axial direction—but not rotate—relative to window tube 30.

During the act of preparing the auto-injector 10 for use, the linear movement of guard 38 downward along the longitudinal axis 46 is induced by applying an opposing twisting torque (T) to injection and retraction assemblies 12, 16, respectively, about the axis 46.

The result of the twisting torque (T) on retraction assembly 16 is described with reference to FIGS. 1, 2, 8, and 9.

Referring to FIG. 2, guard 38 includes a first linear member 60 defined therein and a first cam surface 62 defined thereon. Injection assembly 12, which will be described in more detail herein below, includes a second linear member 64 and a second cam surface 66 defined thereon, which cooperate, respectively, with first linear member 60 and first cam surface 62 of the guard.

In some embodiments, nose 36 can include one or more first linear members 68 defined thereon (FIG. 5), which cooperate with a corresponding number of second linear members 76 (FIG. 5) defined within guard 38. First and second linear members 68 assure that the axial movement of guard 38 relative to retraction assembly 16 due to twisting torque (T) occurs without binding.

Referring to FIGS. 1, 8, 9 and 10, when the opposing twisting torque (T) is applied to injection and retraction assemblies 12, 16, respectively, cap 80 of injection assembly rotates about longitudinal axis 46 with respect to the inner housing 84. During rotation, cam surface 66 impinges on cam surface 62 thereby imposing a determinate force in the axial direction on guard 38. Guard 38 is prevented from rotation with respect to retraction sub-assembly 52 by the interaction of first and second linear members 60, 64, 68. Rather, the twisting torque (T) is converted by cam surfaces 62, 66 into the downward linear movement of guard 38 along axis 46. The linear movement of guard 38 downward along the longitudinal axis 46 results in the guard 38 and, thus by virtue of the engagement between needle sheath shoulder 28 and guard recess 58, needle sheath 18, being removed from the auto-injector 10, and hypodermic needle 20, respectively.

In some embodiments, first linear member 60 of guard 38 includes a retaining feature 70 (FIG. 1). Retaining feature 70 can be a narrowed area of first linear member 60 configured to form a friction fit with second linear member 64. Rather, retaining feature 70 allows second linear member 64 to slide through first linear member 60 upon the application of a predetermined level of axial force, where the axial force being the resultant force created by the action of the cam surface 62 acting on cam surface 66 under the influence twisting torque (T).

As mentioned earlier, while guard 38 and sub-assembly 52 are prevented from rotating upon the application of twisting torque (T) to the injection and retraction assemblies 12, 16 of the fully-assembled auto-injector 10, portions of injection assembly 12 are allowed to rotate under the influence of twisting torque (T). Advantageously, this rotation of portions of injection assembly 12 is used by the present disclosure to disable an activation-prevention device, hereinafter referred to as the "safety", within the injection assembly.

The result of the twisting force (F) on injection assembly 12 is described with reference to FIGS. 8 through 15.

Figure 10:
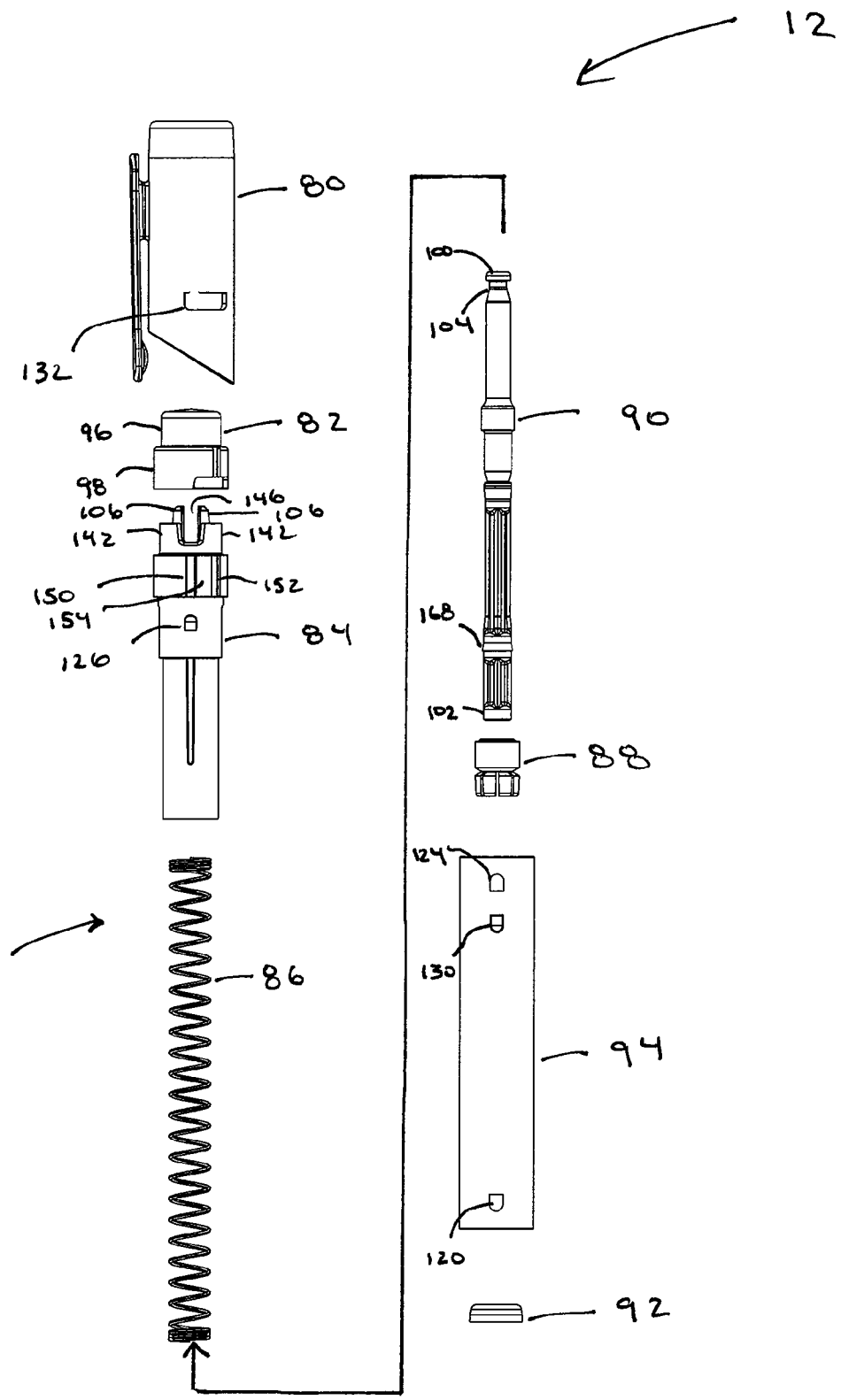
FIG. 10 is an exploded view of an exemplary embodiment of an injection assembly according to the present disclosure.
Figure 11:
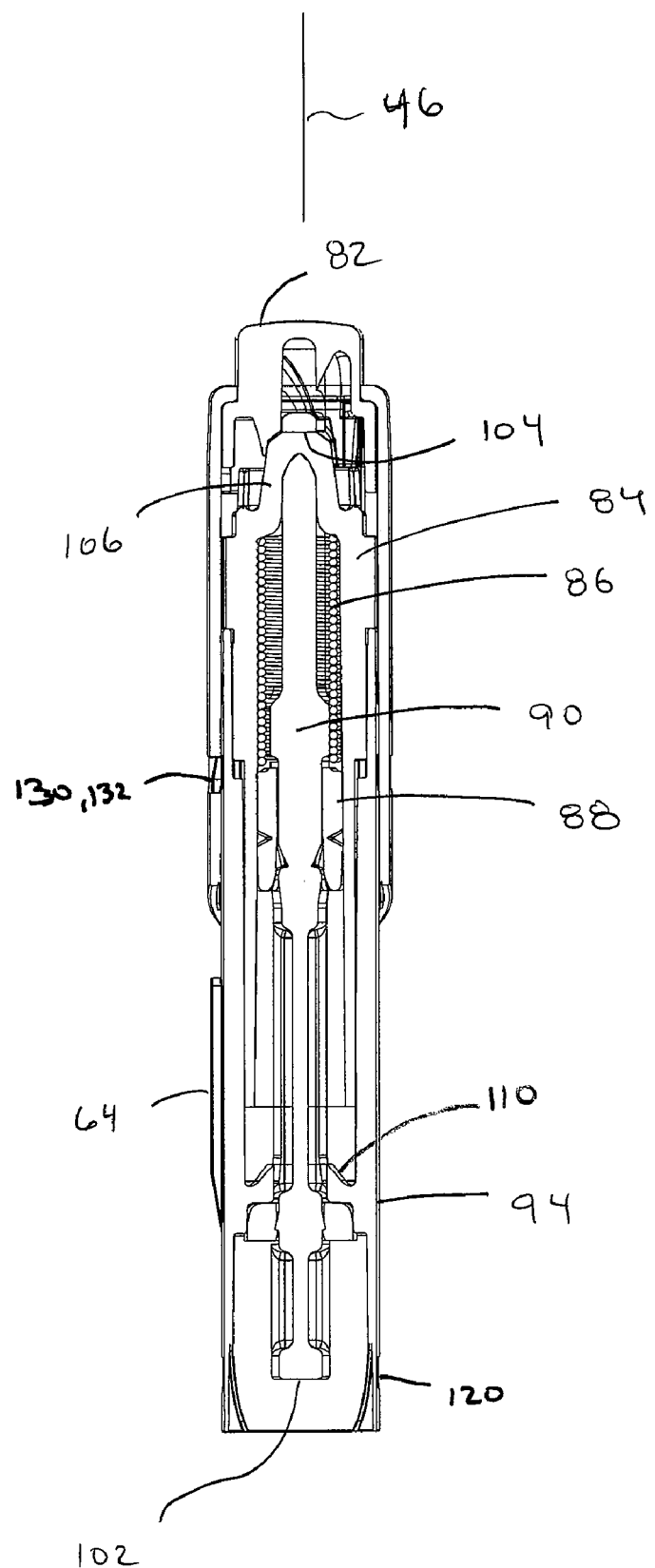
FIG. 11 is a first cross sectional view of the injection assembly of FIG. 10 in an assembled, unfired state.
Figure 12:
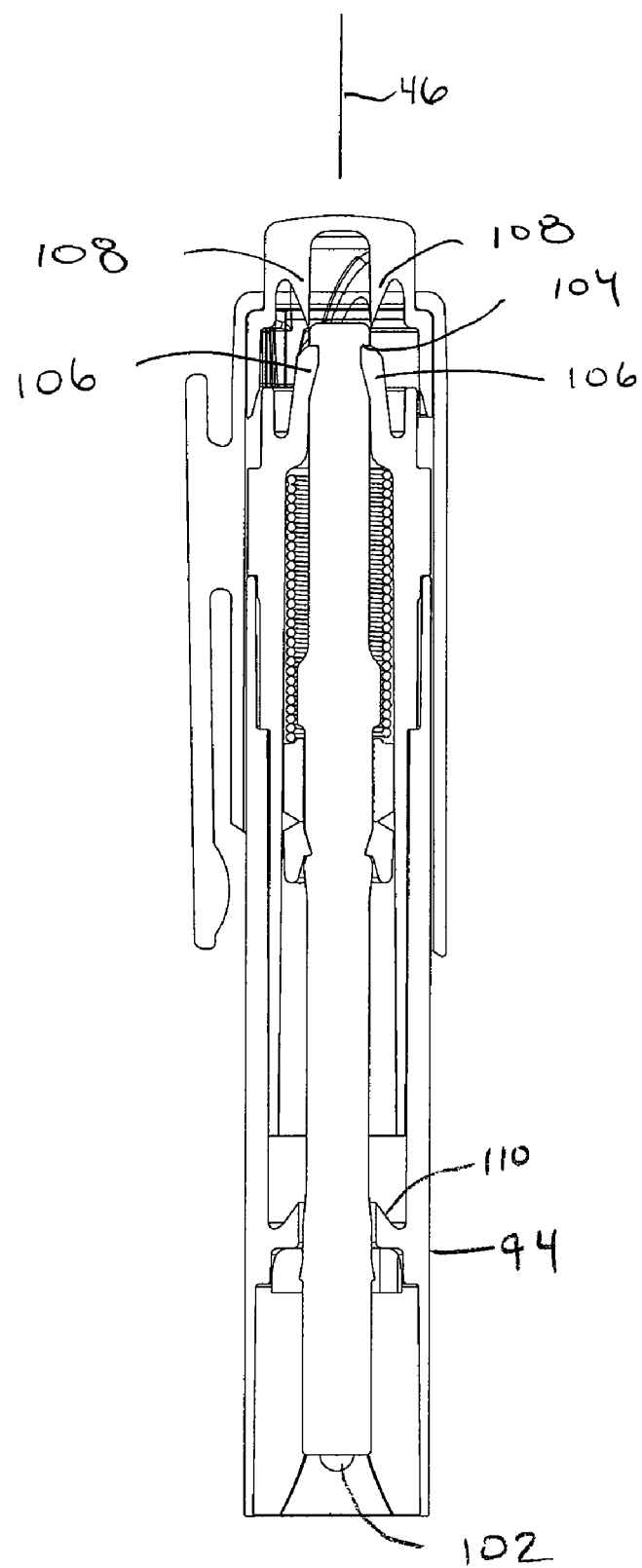
FIG. 12 is a second cross sectional view of the injection assembly of FIG. 10 in an assembled, unfired state taken orthogonal to the view of FIG. 11.

Referring to FIGS. 10 and 11, injection assembly 12 includes a cap 80, an activation button 82, an inner housing 84, an injection spring 86, a coupling 88, a plunger rod 90, a syringe ring 92, and a mid-housing 94.

In some embodiments, plunger rod 90 is fabricated of a highly rigid material that can tolerate tensile and shear stresses indefinitely without distortion or fracture. Inner housing 84 is, in some embodiments, an injection molded plastic component formed of a strong, yet resilient material, e.g., thermoplastic materials such as, but not limited to, poly-carbonate or copolyester.

Figures 13, 14, 15:
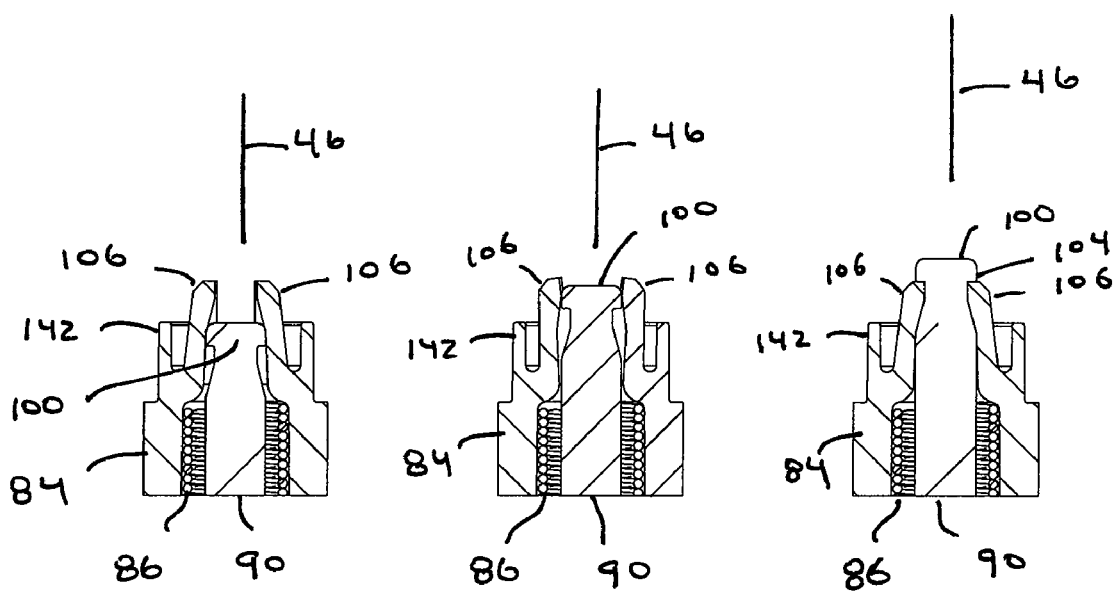
FIGS. 13 through 15 illustrate a partial sectional view of the inner housing of the injection assembly of FIG. 10 during installation of a plunger rod.
Figure 16:
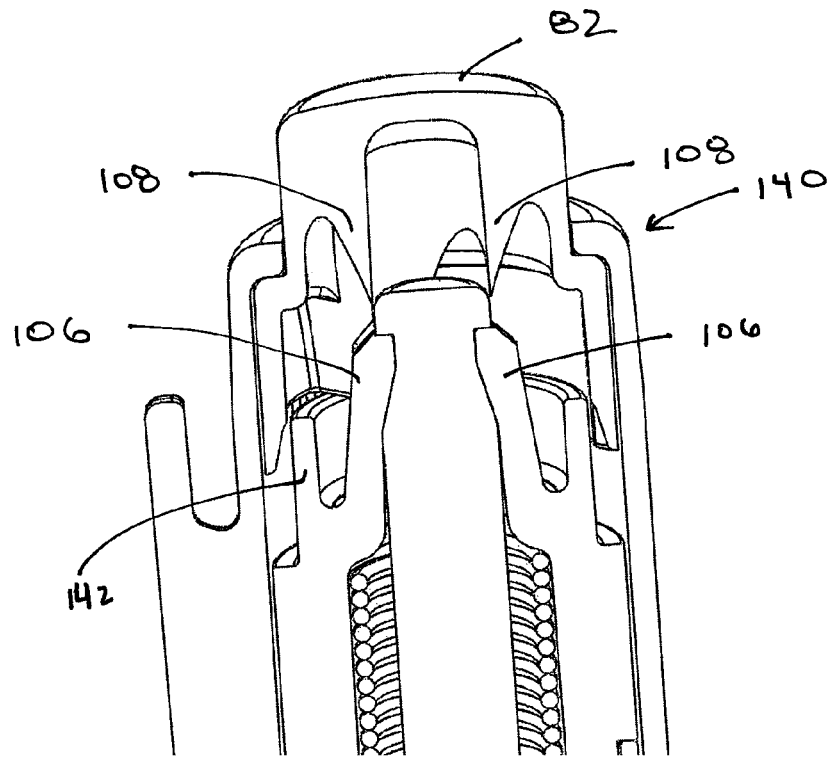
FIG. 16 is a first sectional view of the injection assembly of FIG. 10 having an activation-prevention feature in a "safe" or "on" position.

The material properties of inner housing 84 are chosen to allow for radial flexure of the plunger rod support features 106 so those features can deflect resiliently for installation and controlled release of the plunger rod 90, but also to provide dimensional stability under high stress compressive and shear loading conditions for extended periods of time and under a wide range of environmental conditions. FIGS. 13, 14 and 15 and more detailed descriptions to follow more particularly illustrate the installation of plunger rod 90 relative to support features 106 of inner housing 84.

Referring to FIG. 10, during assembly at the factory, button 82 is placed within cap 80 so that an upper portion 96 of the button protrudes from the cap and a lower portion 98 of the button is retained within the cap. Button 82 is received within cap 80 so that the button can move with respect to the cap in a direction parallel to axis 46, but cannot rotate with respect to the cap about the axis 46. In some embodiments, button 82 and cap 80 can be secured to one another via a key and keyway arrangement (not shown).

Referring still to FIG. 10, lower portion 98 of button 82 extends inwardly to cap 80. When forcibly moved downward along axis 46, features within lower portion 98 are configured to selectively disengage the plunger rod 90 from engagement with inner housing 84 in order to release the energy in injection spring 86 and propel plunger rod 90 downward along axis 46 by way of coupling 88. In the illustrated embodiment, plunger rod 90 includes a locking end 100 and a driving end 102. Locking end 100 includes a shoulder 104 for selective engagement with plunger rod support features 106 of inner housing 84. Driving end 102 is configured to act on piston 24 of medicine cartridge 14 as will be described in detail below.

Injection spring 86 is disposed within inner housing 84 and about plunger rod 90 and the injection spring is selectively and drivingly engaged to the plunger rod via coupling 88.

Inner housing 84 includes one or more selectively releasable plunger rod support members 106 that engage shoulder 104 of plunger rod 90. During assembly, as best seen in FIGS. 13 through 15, locking end 100 is inserted through support members 106 upwardly along axis 46 so as to cause the support members to resiliently flex or bias radially outward from a first state (FIG. 13) to a second state (FIG. 14). Once shoulder 104 clears support members 106, the support members resiliently return to the first state (FIG. 15), thereafter retaining plunger rod 90 in a cocked position with injection spring 86 captured in a fully-energized condition.

Returning to FIGS. 10 through 12, activation button 82 includes one or more releasing surfaces 108 (two shown) configured as part of lower portion 98. Activating force applied to activation button 82 downward along axis 46 causes releasing surfaces 108 to engage cooperative surfaces of support members 106. The interaction of releasing surfaces 108 on support members 106 pry the locking members radially outward away from one another to the second state such that shoulder 104 is released or disengaged from inner housing 84.

Upon release of shoulder 104 from inner housing 84, the stored energy in spring 86 propels plunger rod 90 downward along axis 46. As the plunger rod 90 moves downward under the influence of the injection spring 86, driving end 102 engages piston 24 of medicine cartridge 14 to force syringe cartridge 14 to translate downward until the hypodermic needle 20 is inserted into the tissue at the injection site. At a prescribed distance of forward travel, corresponding to the specified needle insertion depth, the leading end of syringe guide 32 impacts nose 36 or, when present damper pad 42. Once the leading edge of syringe guide 32 impacts nose 36, downward movement of syringe cartridge 14 and syringe guide 32 ceases. In addition, as the plunger rod 90 moves downward under the influence of the injection spring 86, retraction spring 34 becomes energized in a known manner. Continued movement of the plunger rod 90 under the influence of the still-energized injection spring 86 causes liquid medicament from medicine compartment 22 to flow through the hypodermic needle 20 and into the injection site.

As injection spring 86 propels plunger rod 90 downward along axis 46, coupling 88 eventually slidably abuts a decoupling surface 110 defined within mid-housing 94. The force of injection spring 86 upon coupling 88 causes the coupling to engage decoupling surface 110 so that the coupling flares open and disengages from its radial interference engagement with plunger rod 90. The disengagement of coupling 88 from plunger rod 90 terminates the influence of injection spring 86 on plunger rod 90 and allows the plunger rod, syringe guide 32, and syringe cartridge 14 (less the needle sheath which was removed prior to use) to be moved upward along axis 46 by the action of the now energized retraction assembly 16.

Auto-injector 10 can be configured to inject medicament from cartridge 14 intramuscularly, subcutaneously and/or intradermally. For example, decoupling surface 110 can be secured in injection assembly 12 for movement along axis 46. Movement of decoupling surface 110 axially relative to other inner housing features changes the point at which coupling 88 engages the decoupling surface thereby uncoupling injection spring 86 from plunger rod 90.

As thus described, the action of coupling 88 and decoupling surface 110 are substantially as described in co-pending U.S. application Ser. No. 11/296,973, the entire contents of which are incorporated herein by reference.

Figures 8A, 8B, 8C:
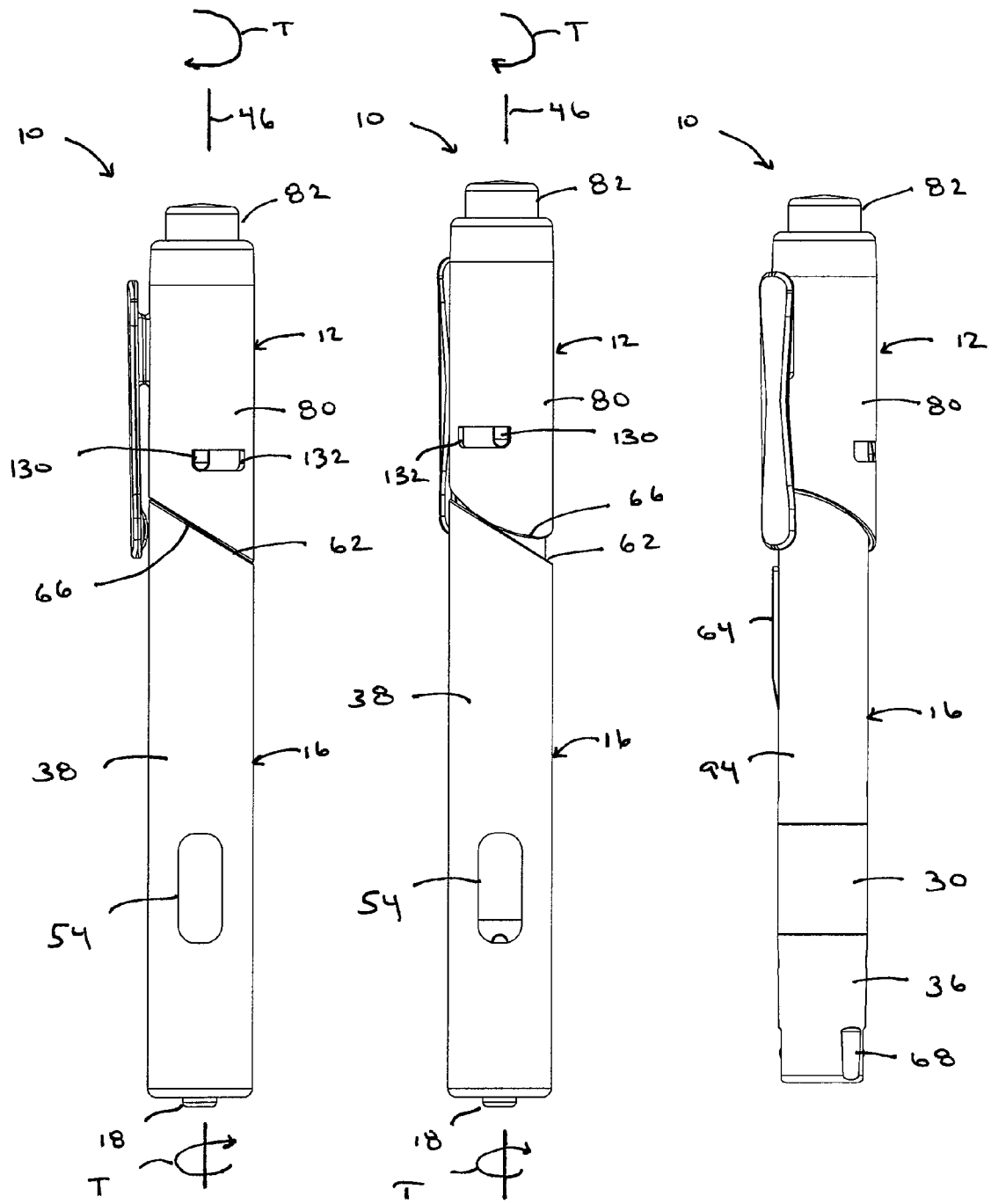
FIG. 8(A) is a side view of the automatic injection and retraction device of FIG. 1 before application of a twisting torque (T) to the injection and retraction assemblies.
FIG. 8(B) is a side view of FIG. 8A after application of the twisting torque (T) and the guard has been disengaged from its home position.
FIG. 8(C) is a side view of FIG. 8B after the twisting torque (T) has been applied, the guard has been removed, and the auto-injector is ready to use.
Figure 9:
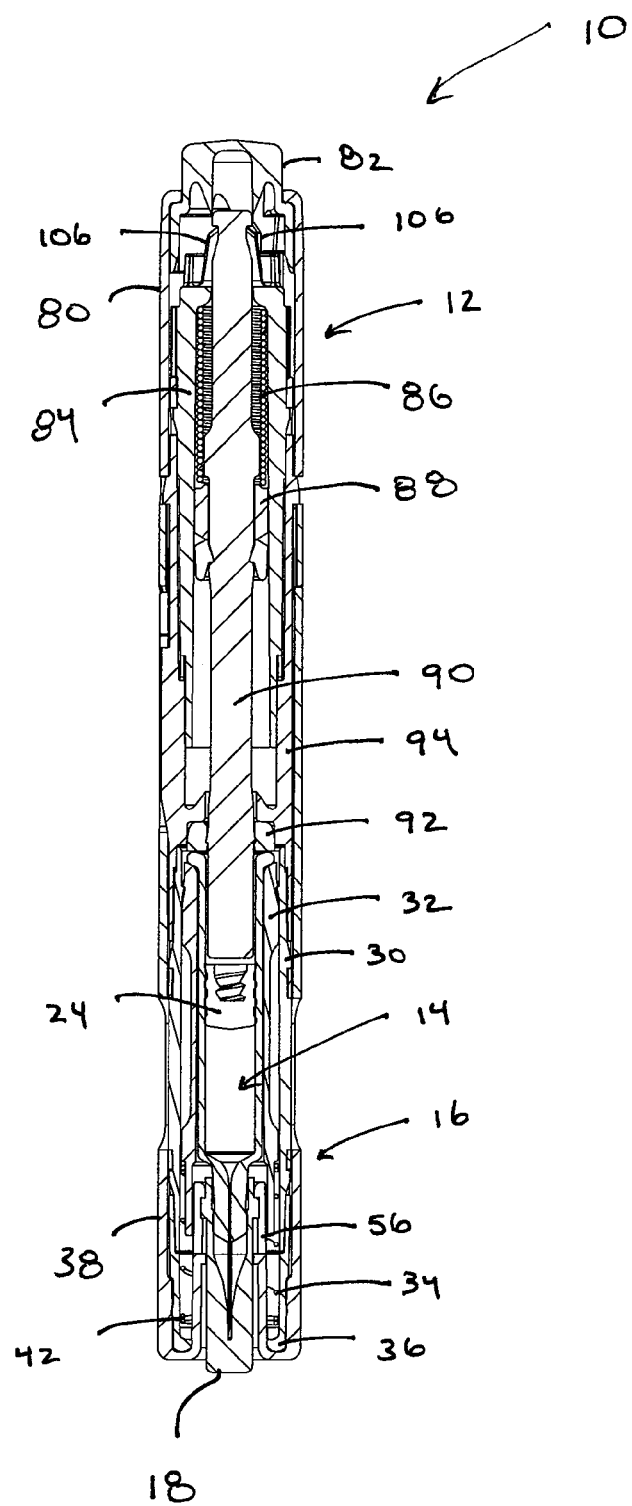
FIG. 9 is a sectional view depicting the device in the state described in FIG. 8(C) taken along line 9-9.

Referring to FIG. 8, and returning to the result of the twisting torque (T) applied on injection and retraction assemblies 12, 16, mid-housing 94 is connected to window tube 30 of retraction assembly 16 so that the mid-housing and the window tube cannot rotate with respect to one another about axis 46. For example, mid-housing 94 can include one or more openings 120 that mate with a corresponding number of tabs 122 defined on window tube 30 (FIG. 5). Further, mid-housing 94 is connected to inner housing 84 so that the mid-housing and the inner housing can not rotate with respect to one another about axis 46. For example, mid-housing 94 can include one or more openings 124 that mate with a corresponding number of tabs 126 defined on inner housing.

In a preferred embodiment as depicted in FIG. 11, cap 80 is permanently positioned over inner housing 84 and mid-housing 94 during assembly at the factory. After such assembly, cap 80 is secured to mid-housing 94 so that the cap cannot move along axis 46, but can rotate under the influence of the applied twisting torque (T) with respect to inner housing 84 and mid-housing 94 about the axis 46. For example, mid-housing 94 can include one or more guides 130 defined thereon, while cap 80 can include a corresponding number of radially disposed tracks 132 defined thereon. Guides 130 are maintained in tracks 132 so that the cap cannot move along axis 46, but can rotate with respect to inner housing 84 and the mid-housing 94 about the axis 46 as during the process of disabling the safety mechanism.

Thus, when twisting torque (T) is applied to retraction assembly 16 via guard 38 and injection assembly 12 via cap 80, the following movements occur: cap 80 and button 82 rotate together about axis 46 relative to inner housing 84 and mid-housing 94. Similarly, guard 38, concurrently, and by virtue of the action of cap cam surface 66 acting on guard cam surface 62, translates downward relative to mid-housing 94 along axis 46 under the piloted constraint of guides 60 and 64.

In sum, and returning for a moment to FIGS. 8 and 9, the twisting torque (T) results in cap 80 and button 82 rotating together about axis 46 with respect to guard 38, retraction sub-assembly 52, and inner housing 84 and mid-housing 94. The rotation of cap 80 with respect to guard 38 results in cam surfaces 62, 66 converting the twisting torque (T) into a downward resultant linear force acting upon the guard 38 along axis 46 due to the interaction of first and second linear members 60, 64, 68. As guard 38 moves downward along axis 46 with respect to retraction sub-assembly 52, the guard and needle sheath 18 are disengaged from auto-injector 10 and needle 20, respectively.

Accordingly, cap 80 and button 82 form an activation sub-assembly 72 configured so that the cap and button are locked together for rotation about axis 46 but allow button 82 to move axially along axis 46 within cap 80. Further, inner housing 84, injection spring 86, plunger rod 90, coupling 88, mid-housing 94, and syringe ring 92 together form an injection sub-assembly 74. The components of injection sub-assembly 74 are locked together for rotation about axis 46 but allow spring 86 to move plunger rod 90, coupling 88, and syringe ring 92 axially along axis 46 within mid-housing 94. Thus, when twisting torque (T) is applied to retraction assembly 16 via guard 38 and injection assembly 12 via cap 80, the following movements occur: activation sub-assembly 72 rotate together about axis 46 relative to injection and retraction sub-assemblies 52, 74. Similarly, guard 38, concurrently, and by virtue of the action of cap cam surface 66 acting on guard cam surface 62, translates downward relative to retraction sub-assembly 52.

Figure 18:
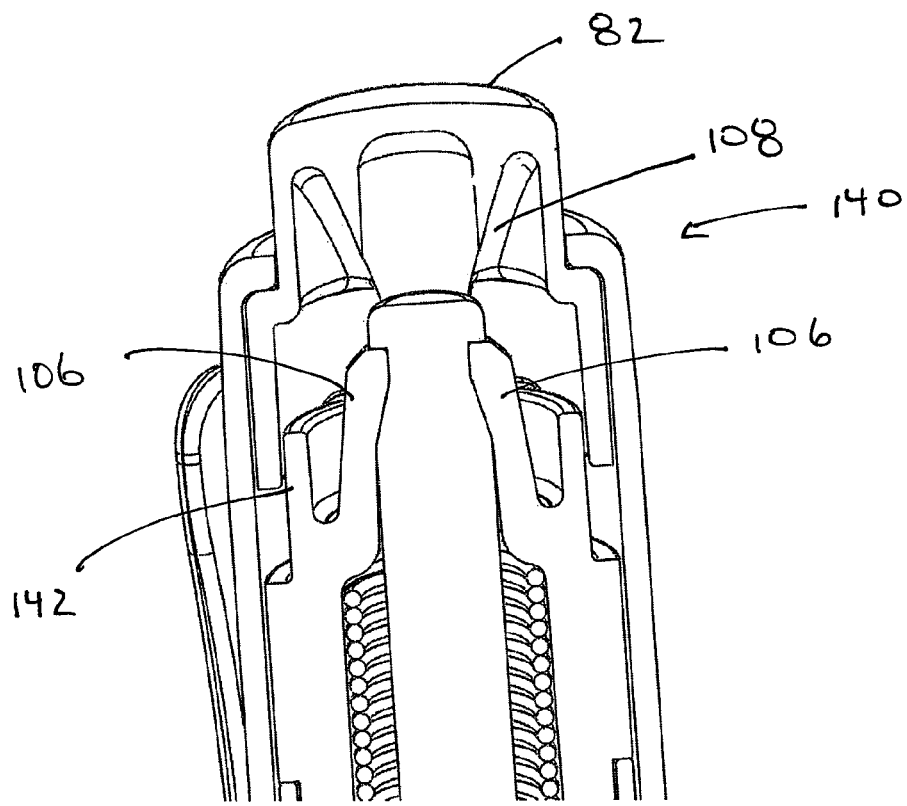
FIG. 18 is a first sectional view of the injection assembly of FIG. 16 having the activation-prevention feature in an "armed" or "off" position.
Figure 19:
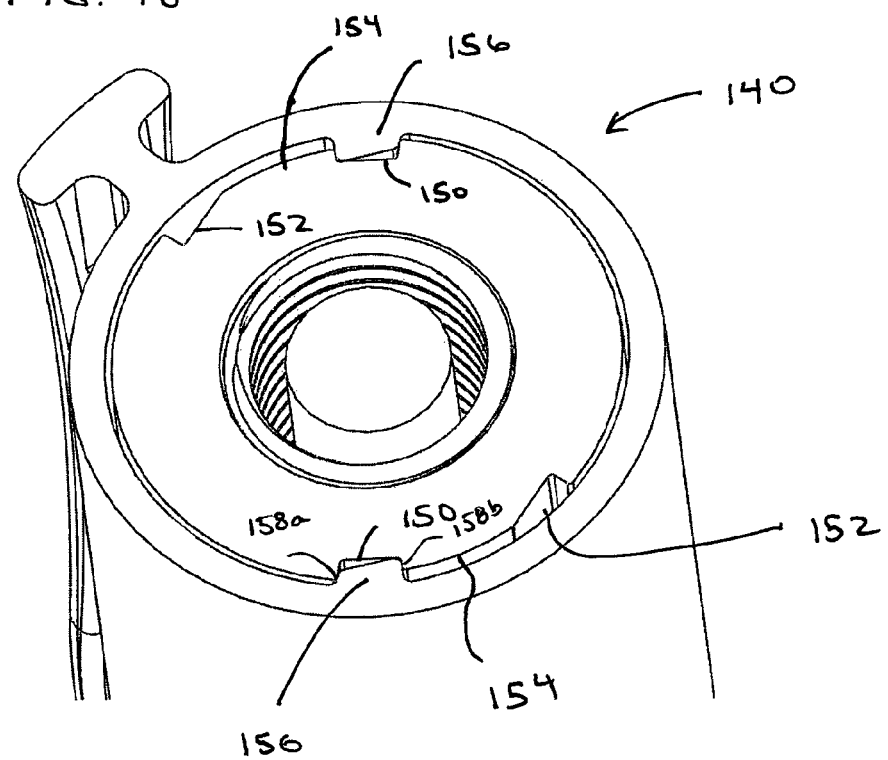
FIG. 19 is a second sectional view of the injection assembly of FIG. 16 having the activation-prevention feature in the "armed" or "off" position.
Figure 20:
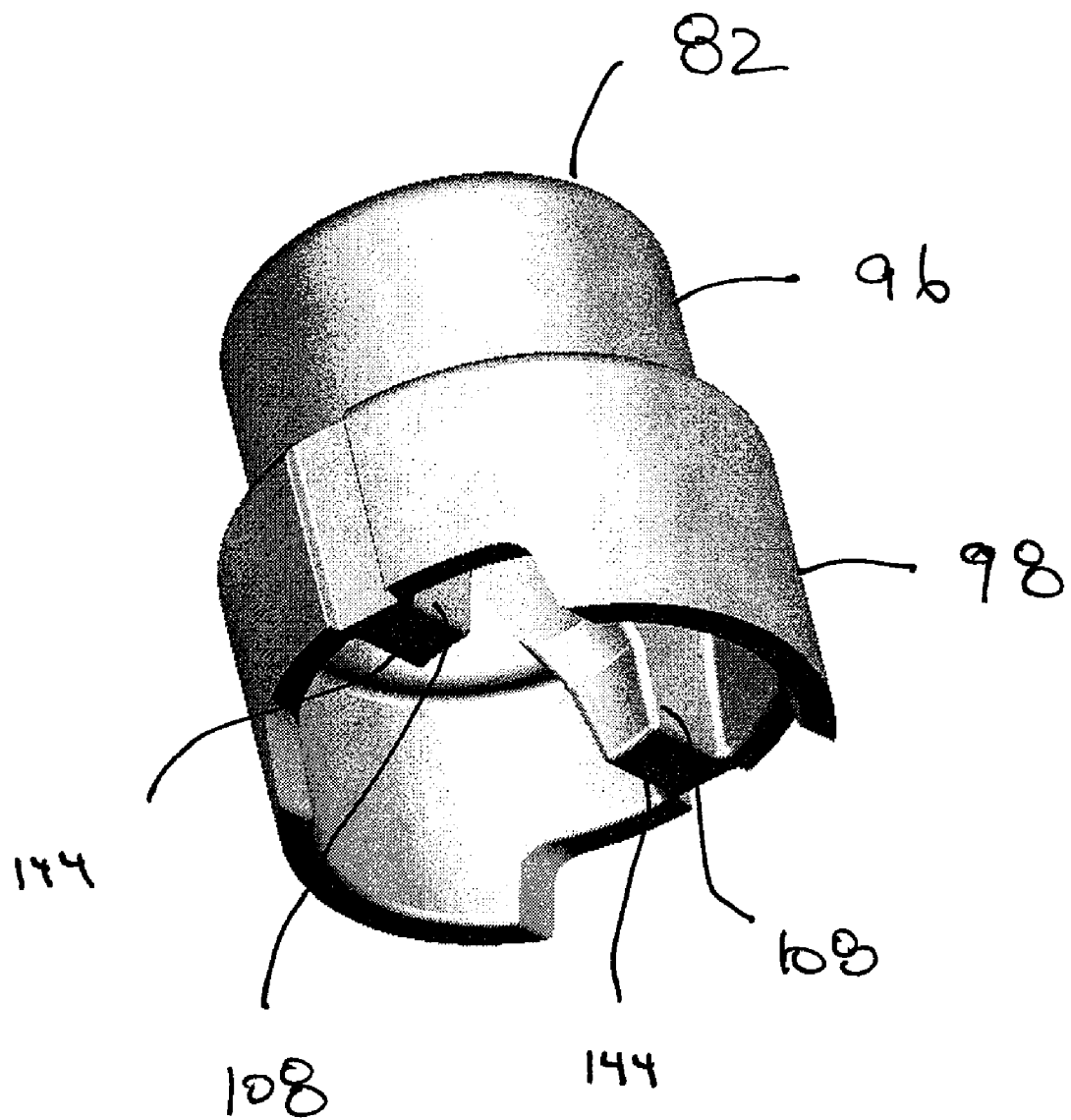
FIG. 20 is a bottom perspective view of an exemplary embodiment of an activation button according to the present disclosure.

Referring to FIGS. 18 and 19, advantageously, injection assembly 12 includes an activation-prevention or "safety" feature 140, which can mitigate inadvertent depression of activation button 82 and, thus, can prevent premature activation of injection assembly 12. Moreover, in some embodiments, activation-prevention feature is disabled (namely, auto-injector 10 is armed) by the application of twisting torque (T) discussed above.

Activation-prevention feature 140 is described with reference to FIGS. 16 through 21. Inner housing 84 includes a safety ring 142 integrally formed thereon, wherein the safety ring includes a pair of activation slots 146 defined therethrough. Activation slots 146 are radially aligned with plunger rod support features members 106 for reasons discussed immediately below.

As discussed above, activation button 82 includes releasing surfaces 108, which are configured to expand plunger rod support members 106, when the button is pressed downward along axis 46 during device activation. Releasing surfaces 108 have a bottom rim 144. When activation-prevention feature 140 is in a "safety on" position (FIGS. 16 and 17), button 82 is radially orientated so that bottom rim 144 abuts with safety ring 142. Thus, in the "safety on" position, safety ring 142 prevents depression of button 82 by providing an axial interference with the button. Axial interference between safety ring 142 and bottom rim 144 represents an impediment to axial travel of button 82 in the "safety on" position of activation-prevention feature 140.

However, when activation-prevention feature 140 is in an "armed" or "safety off" position (FIGS. 18 and 19), button 82 is positioned so that bottom rim 144 is radially aligned with activation slots 146. Thus, in the "armed" or "safety off" position, safety ring 142 allows depression of button 82 by eliminating the axial interference with the button. More particularly, activation slots 146 are sized and positioned to receive releasing surfaces 108 therein when button 82 is pressed downward along axis 46. As button 82 is pressed downward along axis 46, releasing surfaces 108 pass into activation slots 146 and force the plunger rod supports 106 radially outward.

Advantageously, button 82 is rotated along with cap 80 during the application of twisting torque (T). Thus, the same twisting torque (T) that results in removal of guard 38 and needle sheath 18 concurrently moves activation-prevention feature 140 to the "armed" or "safety off" position.

Further, and as discussed above with respect to FIGS. 8 and 9, mid-housing 94 includes guides 130 that are maintained in tracks 132 of cap 80. Guides 130 provide the user with a visual indication of the status of activation-prevention feature 140. Thus, activation-prevention feature 140 is in the "safety on" position in FIG. 8, and in the "armed" or "safety off" position in FIG. 9.

Figure 17:
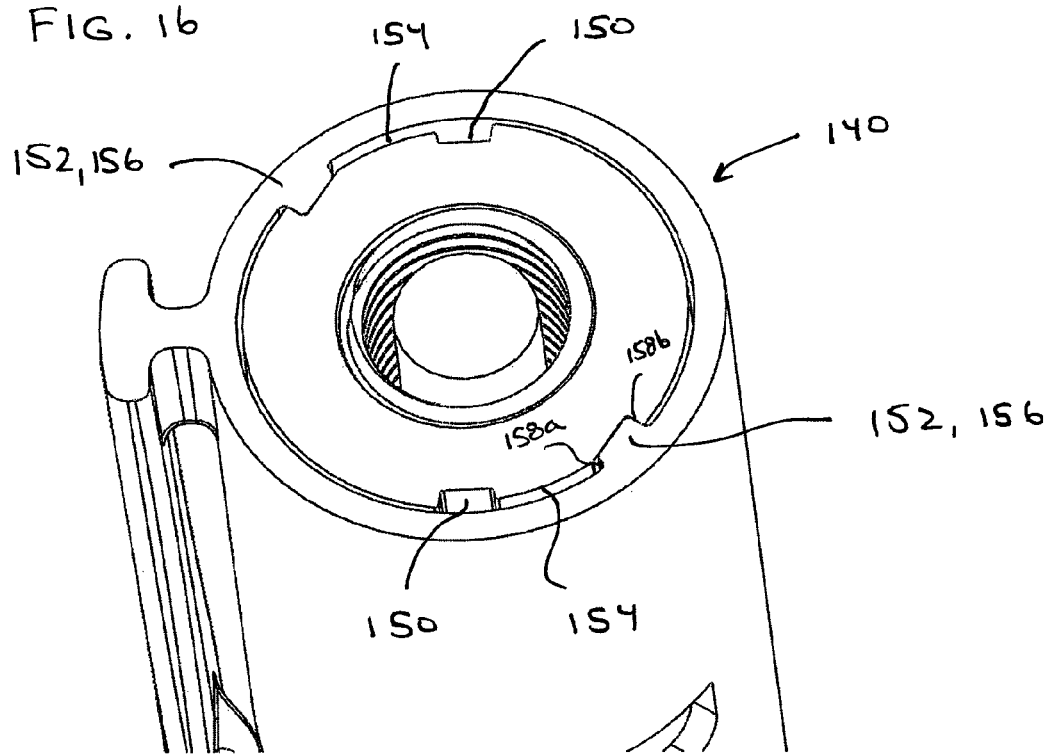
FIG. 17 is a second sectional view of the injection assembly of FIG. 10 having an activation-prevention feature in the "safe" or "on" position.
Figure 21:
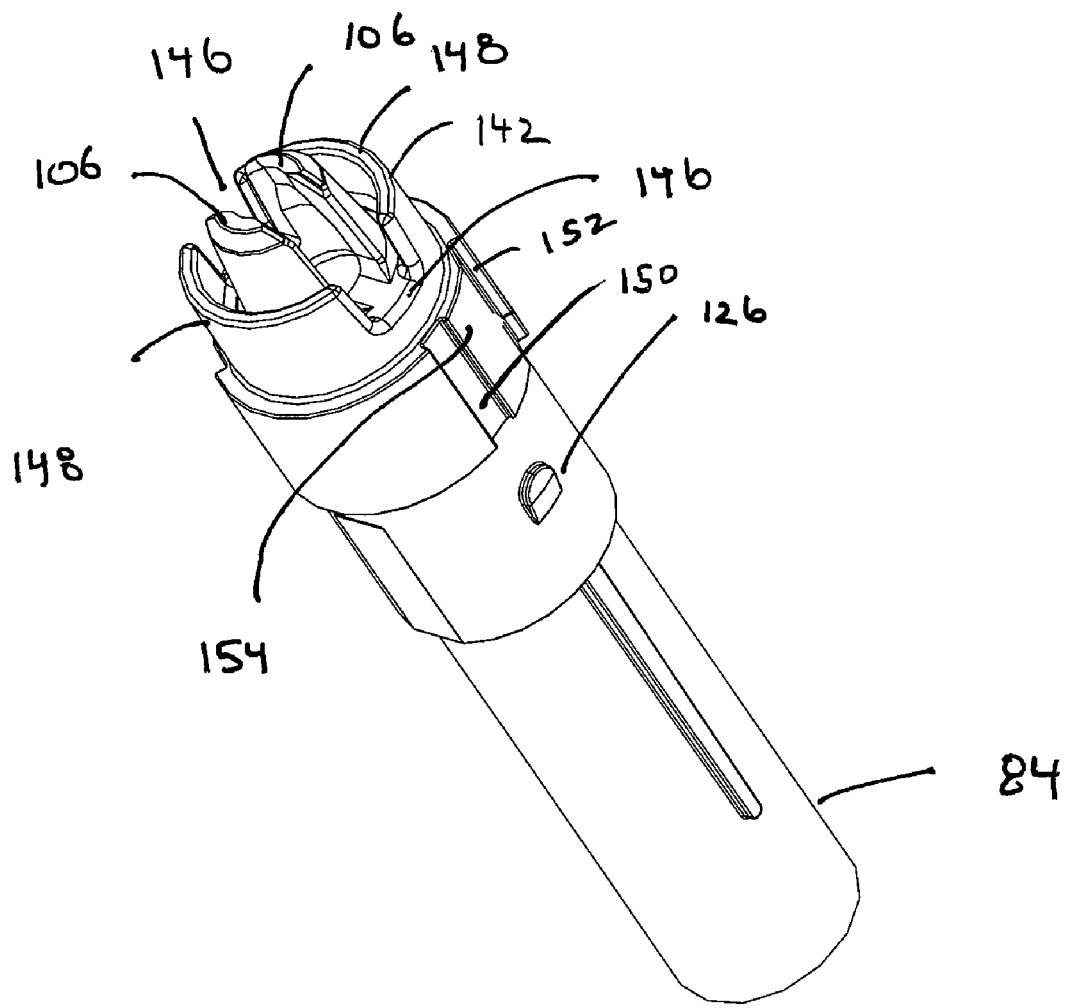
FIG. 21 is a top perspective view of an inner housing according to the present disclosure.

In some embodiments, at the end of the allowable rotational travel due to twisting force (F), cap 80 can be configured to snap into a permanent "safety off" position. For example, inner housing 84 can include one or more lock grooves 150 (two shown) that cooperate with one or more safe grooves 152 by a cam surface 154 as seen in FIGS. 17, 19, and 21. Cap 80 includes a corresponding number of safety lock tabs 156 defined therein as seen in FIGS. 17 and 19.

In the "safety on" position of activation-prevention feature 140, lock tabs 156 are received in safe grooves 152. In the permanent "safety off" or "armed" position of activation-prevention feature 140, lock tabs 156 are received in lock grooves 150. Lock tabs 156 have a leading edge 158a and a trailing edge 158b, wherein the leading edge has a gradual inclined plane allowing the locking tab to easily climb out of its home position in grooves 152 in the inner housing 84. As cap 80 is rotated, due to twisting torque (T), lock tabs 156 escape their home position in grooves 152 and ride in an interference engagement with cam surface 154, causing the cap 80 to resiliently bias radially outward until the lock tabs are rotated fully into position and are received in lock grooves 150. Since lock slot surface 150 presents an abrupt stepped engagement cooperating with the trailing surface 158b, once locking tabs 156 are engaged in the receiving grooves 150, the interference provides a significant resistance to an opposite twisting force preventing the lock tabs 156 from being disengaged from lock grooves 150. Once the locking tabs 156— and thus by cooperation the activation-prevention feature 140—are disabled, cap 80 cannot be rotated in the opposite direction such that the activation-prevention feature therefore cannot be moved back to the "safety on" position.

The operation of auto-injector 10 upon activation will be described in more detail with reference to FIGS. 22 through 25. More particularly, auto-injector 10 includes, in some embodiments, a temporary engagement feature 160. Temporary engagement feature 160 engages plunger rod 90 to syringe guide 32 for an initial portion of the stroke of the plunger rod. In this manner, auto-injector 10 is configured to first move syringe guide 32 downward along axis 46 before moving piston 24 within medicine compartment 22. Thus, auto-injector 10 can first extend needle 20 from retraction device 16 before dispensing the liquid medicament from medicine compartment 22.

Temporary engagement feature 160 includes plunger rod 90, syringe ring 92, and first and second bore regions 162,164 defined in mid-housing 94.

Figure 23A:
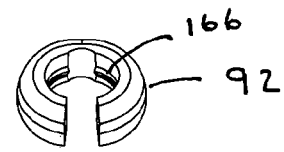
FIG. 23A is a top perspective view of a syringe ring for use with the temporary engagement feature of FIG. 22, where the syringe ring is shown in an unconstrained state.
Figure 23B:
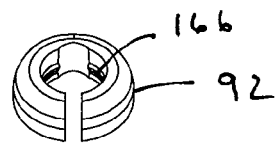
FIG. 23B is a top perspective view of the syringe ring of FIG. 23A in a constrained state.

Syringe ring 92 is elastically moveable between an unconstrained state (FIG. 23A) and a constrained state (FIG. 23B). Syringe ring 92 includes an internal rim 166 that selectively engages with an external rim 168 on plunger rod 90 when the ring is in the constrained state, but releases the external rim when the ring is in the unconstrained state.

Figure 22:
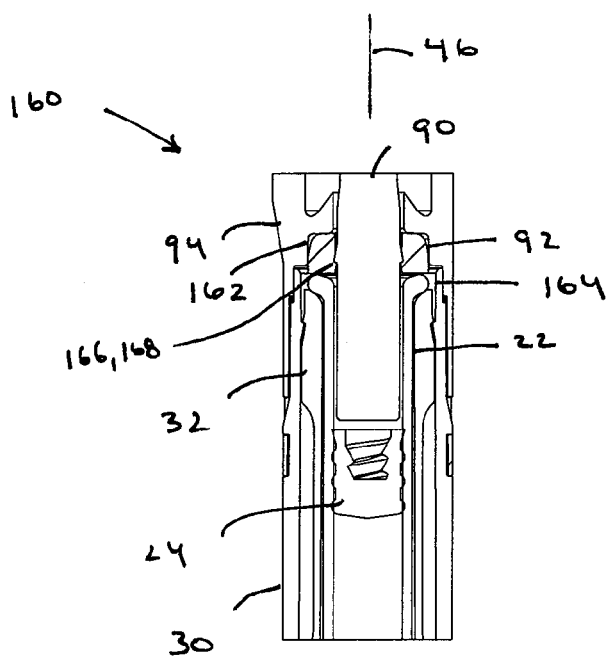
FIG. 22 is a partial sectional view of an exemplary embodiment of an automatic injection and retraction device having a temporary engagement feature according to the present disclosure, before activation.

Before activation of auto-injector 10 as shown in FIG. 22, syringe ring 92 is maintained in the constrained state by first bore region 162. Thus, before activation, syringe ring 92 is drivingly engaged to plunger rod 90 so that the syringe ring 92 abuts a top end of medicine compartment 22. Here, plunger rod 90 is not in contact with piston 24 of pre-filled syringe cartridge 14.

Figure 24:
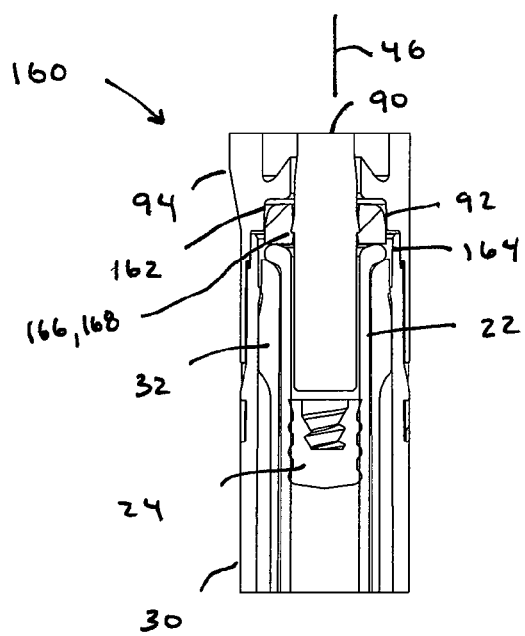
FIG. 24 is a partial sectional view the automatic injection and retraction device of FIG. 22 immediately after activation and during temporary engagement between plunger rod and syringe ring.

Once activated, plunger rod 90 moves downward along axis 46. The downward movement of plunger rod 90 causes syringe ring 92 to also move downward due to the engagement between internal and external rims 166, 168. As a result of the downward movement of ring 92, the ring acts on medicine compartment 22 and, thus, moves syringe guide 32 and cartridge 14 downward for an initial portion of the stroke of the plunger rod 90 (FIG. 24). During this initial portion of the stroke of plunger rod 90, syringe ring 92 ensures that the plunger rod 90 is not in contact with piston 24 of pre-filled syringe cartridge 14.

Figure 25:
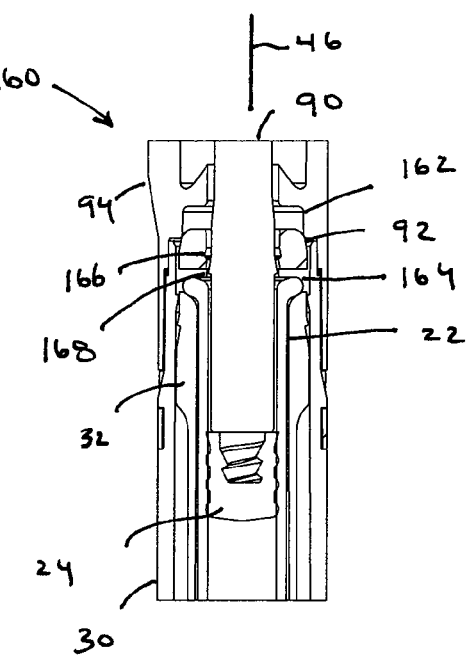
FIG. 25 is a partial sectional view the automatic injection and retraction device of FIG. 22 after temporary engagement between plunger rod and syringe ring has ceased.

Once syringe ring 92 travels a predetermined distance along the longitudinal axis 46, namely to the point where the ring is free of first bore 162 and is located at second bore 164, the ring elastically returns to its unconstrained state. More particularly, syringe ring 92 opens up once the ring is located at second bore 164 so that the ring is no longer drivingly engaged to plunger rod 90 (FIG. 25). Once syringe ring 92 is opened, plunger rod 90 continues to move downward due to the force of injection spring 86 on coupling 88 so that the plunger rod 90 contacts piston 24 of pre-filled syringe cartridge 14 to insert the needle and dispense the liquid medicament in the manner discussed above.

In some embodiments, auto-injector 10 can also include a retaining feature 170 for syringe guide 32 as also shown in FIGS. 22, 24, and 25.

Retaining feature 170 is configured to secure syringe guide 32 in a predetermined position before assembly of retraction assembly 16 to injection assembly 12. In this manner, syringe guide 32 is temporarily retained in a desired position within the retraction assembly 16.

Retaining feature 170 includes a tab 172 defined on window tube 30 and a rim 174 defined in syringe guide 32. During assembly of retraction assembly 16, syringe guide 32 is inserted into window tube 30 until rim 174 engages tab 172. Once auto-injector 10 is fully assembled and activated, the force of injection spring 86 on syringe guide 32 via temporary engagement feature 160 is sufficient to overcome the engagement between tab 172 and rim 174 so that the syringe guide can move downward along axis 46 as desired.

In some embodiments of the present disclosure, and notwithstanding any self-retracting function of retraction assembly 16, it may be desirable on the part of the user to reinstall the guard 38 onto the auto-injector 10 after use. Thus, guard 38 can be configured to recap auto-injector 10 so that needle shield 18 re-encapsulates the used hypodermic needle 20 in a rigid (due to guard 38) and sealed (due to sheath 18) enclosure, making the device safe for disposal without exposing others to the dangers of inadvertent needle stick injury and/or blood-borne pathogens. In this embodiment, and during the re-capping action, guard 38 acts as a holder for sheath 18.

Figure 27:
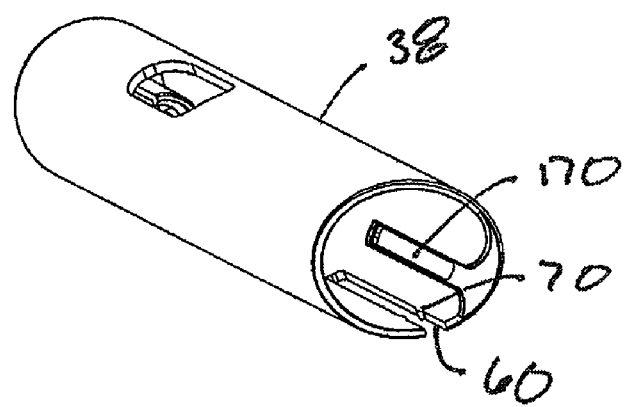
FIG. 27 provides an inward detail of the features described in FIG. 26.
Figure 26:
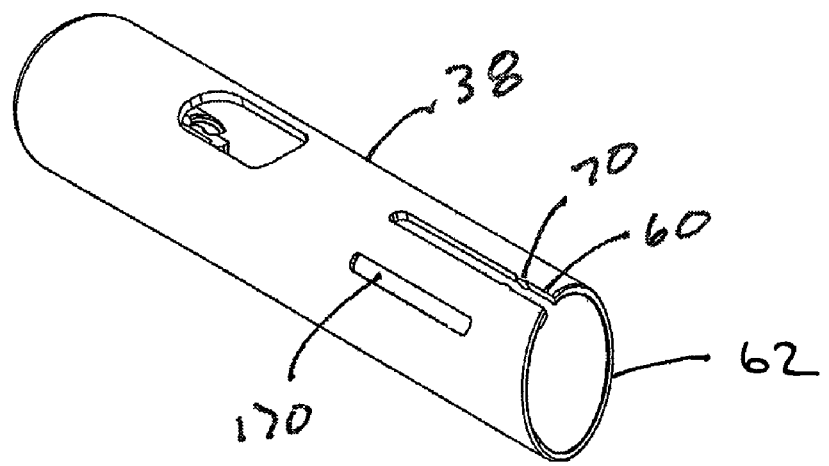
FIG. 26 provides a pictorial detailed view of cooperative features enabling the permanent re-assembly of the guard and auto-injector.

Referring to FIGS. 26 and 27, guard 38 and mid-housing 94 can include features 170 and 64, respectively to create a permanent snap-fit connection therebetween upon reinstallation of the guard after use. In the illustrated embodiment, feature 170 includes an inwardly disposed, funneled lead-in surface which facilitates easy alignment of the male feature 64 with the receiving feature 170 as the guard approaches its fully re-attached position. Alignment is further facilitated by the cooperative and preferential alignment of cam surfaces 66 and 62 as the guard approached its fully reattached position. In this manner, hypodermic needle 20 can be permanently secured and enclosed within needle sheath 18 and needle guard 38 after use.

As described herein, auto-injector 10 is a multi-component device that can be assembled by a manufacturer, a user, or a healthcare provider. Since exemplary embodiments of syringe 10 do not require assembly at the time of manufacture, the present disclosure effectively separates expiry of cartridge 14 from the expiry of auto-injector 10. For example, typical flu vaccines have an expiration date of one year. Thus, the user can maintain a supply of injection and retraction assemblies 12, 16 of the present disclosure, and maintain a separate supply of cartridges 14.

Thus, the drug-laden pre-filled syringe cartridge 14 can be prepared at one location, the components of auto-injector 10 can be manufactured at a separate location and the assembly of the auto-injector and syringe cartridge can occur at a different location and/or at a later time.

For example in one embodiment of the present disclosure, a kit can be provided that includes one injection assembly 12, one retraction assembly 16, and a plurality of pre-filled syringe cartridges 14. Here, the plurality of pre-filled syringe cartridges 14 can each contain a different liquid medicament or the same liquid medicament but in varying amounts available for selection (as may be useful in an EMS emergency kit) to quickly install into the auto-injector 10 prior to use.

Further, the present disclosure, due to the separation of auto-injector 10 from cartridge 14, eliminates the need to sterilize the auto-injector as is required in many prior devices. More particularly, the liquid medicament contained within pre-filled syringe cartridge 14 is maintained in its "as manufactured" or sterile condition regardless of the sterility status of the auto-injector assembly. With the present invention, there is therefore no need to ship the drug-filled syringe cartridge assemblies in sterile barrier packaging. Nor is it necessary to sterilize the auto-injector in order to assure sterility of the fluid flow path and drug solution.

Additionally, it has been determined by the present disclosure that the regulatory pathway for attaining market clearance of auto-injector 10, which only requires an already approved cartridge 14 is considerably less expensive and time consuming. As such, auto-injector 10 of the present disclosure facilitates the availability of many more drugs in user-friendly auto-injectors due to an easier and more straightforward regulatory pathway.

It should also be noted that the terms "first", "second", "third", "upper", "lower", "top", "bottom", "upward", "downward" and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

PARTS LIST automatic injection and retraction device 10
injection assembly 12
pre-filled syringe cartridge 14
retraction assembly 16
needle sheath 18
hypodermic needle 20
medicine compartment 22
piston 24
portion 26 of medicine compartment 22
shoulder 28
window tube 30
syringe guide 32
return spring 34
nose 36
guard 38
bottom support surface 40
elastomeric damper pad 42
top support surface 44
longitudinal axis 46
tabs 48
openings 50
retraction sub-assembly 52
sight opening 54
inner housing member 56
recess 58
twisting torque (T)
first linear member 60
first cam surface 62
second linear member 64
second cam surface 66
first linear members 68
retaining feature 70
activation sub-assembly 72
injection sub-assembly 74
second liner member 76
not used 78
cap 80
activation button 82
inner housing 84
injection spring 86
coupling 88
plunger rod 90
syringe ring 92
mid-housing 94
upper portion 96
lower portion 98
locking end 100
driving end 102
shoulder 104
plunger rod support features 106
releasing surfaces 108
decoupling surface 110
not used 112
not used 114
not used 116
not used 118
openings 120
tabs 122
openings 124
tabs 126
not used 128
guides 130
tracks 132
not used 134
not used 136
not used 138
activation-prevention feature 140
safety ring 142
bottom rim 144 slots 146
not used 148
lock grooves 150
safe grooves 152
cam surface 154
safety lock tabs 156
leading edge 158*a*
trailing edge 158*b*
temporary engagement feature 160
first bore region 162
second bore region 164
internal rim 166
external rim 168
retaining feature 170
tab 172
rim 174

What is claimed is:

1. An automatic injection and retraction device having a longitudinal axis, comprising:
    an injection assembly having an activation-prevention feature moveable between an on position and an off position;
    a retraction assembly having a needle guard, said needle guard being removable from said retraction assembly in a direction along the longitudinal axis upon application of a removal force; and
    a pre-filled syringe cartridge having a hypodermic needle with a needle sheath thereon, said retraction assembly being secured to said injection assembly so that said pre-filled syringe cartridge is disposed in said retraction assembly with said needle sheath secured to said needle guard,
    wherein said injection and retraction assemblies are configured so that, upon application of a twisting torque to said injection and retraction assemblies about the longitudinal axis, said activation-prevention feature is configured to move from said on position to said off position simultaneous with applying said removal force to said needle guard.

2. The automatic injection and retraction device as in claim 1, wherein said injection and retraction assemblies have cooperating cam surfaces configured to transmit said twisting torque as said removal force.

3. The automatic injection and retraction device as in claim 1, wherein said activation-prevention feature is configured to prevent movement from said off position to said on position.

4. The automatic injection and retraction device as in claim 1, wherein said retraction assembly, after use, is configured to permanently receive said needle guard having said needle sheath secured thereto so that said hypodermic needle is enclosed within said retraction assembly.

5. The automatic injection and retraction device as in claim 1, further comprising a temporary engagement feature between said injection assembly and a medicine compartment of said pre-filled syringe cartridge so that said injection assembly is configured to move said pre-filled syringe cartridge a predetermined distance along the longitudinal axis without said injection assembly drivingly engaging a piston of said pre-filled syringe cartridge.

6. The automatic injection and retraction device as in claim 5, wherein, after movement of said pre-filled syringe cartridge said predetermined distance, said temporary engagement feature is configured to release from said injection assembly so that said injection assembly is drivingly engaged to said piston of said pre-filled syringe cartridge.

7. An automatic injection and retraction device having a longitudinal axis, comprising:
    an injection assembly having an activation sub-assembly and an injection sub-assembly, said activation sub-assembly being rotatable with respect said injection sub-assembly about the longitudinal axis but not moveable with respect to said injection sub-assembly along the longitudinal axis;
    a retraction assembly having a retraction sub-assembly and a needle guard, said needle guard being moveable with respect said retraction sub-assembly along the longitudinal axis but not rotatable with respect to said retraction sub-assembly along the longitudinal axis; and
    a pre-filled syringe cartridge having a hypodermic needle with a needle sheath thereon, said retraction assembly being secured to said injection assembly so that said pre-filled syringe cartridge is disposed in said retraction assembly with said needle sheath secured to said needle guard,
    wherein said needle guard having said needle sheath secured thereto is removed from said retraction sub-assembly in a direction along the longitudinal axis upon application of a twisting torque to said activation sub-assembly and said needle guard about the longitudinal axis.

8. The automatic injection and retraction device as in claim 7, wherein said injection assembly further comprises an activation-prevention feature moveable between an on position and an off position.

9. The automatic injection and retraction device as in claim 8, wherein said activation-prevention feature is moved from said on position to said off position simultaneously with said needle guard and said needle sheath being moved in said direction upon application of said twisting torque.

10. The automatic injection and retraction device as in claim 8, wherein said activation-prevention feature is configured to prevent movement from said off position to said on position.

11. The automatic injection and retraction device as in claim 7, wherein said retraction sub-assembly, after use, is configured to permanently receive said needle guard having said needle sheath secured thereto so that said hypodermic needle is enclosed within said retraction assembly.

12. The automatic injection and retraction device as in claim 7, wherein said activation sub-assembly comprises an activation button and a cap, said activation button being received in said cap so that said activation button is moveable with respect said cap along the longitudinal axis but not rotatable with respect to said cap along the longitudinal axis.

13. The automatic injection and retraction device as in claim 7, wherein said pre-filled syringe cartridge further comprises a medicine compartment permanently affixed to and in fluid communication with said hypodermic needle and a piston slidably received in said medicine compartment.

14. The automatic injection and retraction device as in claim 13, wherein said injection sub-assembly comprises a housing component, a plunger rod, and a syringe ring, said housing component having a first bore and a second bore, said plunger being secured to said syringe ring when said syringe ring is received in said first bore so that said plunger rod drivingly engages said medicine compartment but not said piston, said plunger rod being free of said plunger rod when said syringe ring is received in said second bore so that said plunger rod drivingly engages said piston but not said medicine compartment.

15. The automatic injection and retraction device as in claim 7, wherein said retraction sub-assembly comprises one or more first linear members cooperate with a corresponding number of second linear members disposed on said needle guard so that said needle guard is moveable with respect said retraction sub-assembly along the longitudinal axis but not rotatable with respect to said retraction sub-assembly along the longitudinal axis.

16. The automatic injection and retraction device as in claim 7, wherein said needle guard comprises a sight opening defined therethrough and said retraction sub-assembly is made of substantially transparent material so that a user has a direct line of sight to said pre-filled syringe cartridge.

17. The automatic injection and retraction device as in claim 7, wherein said needle guard and said cap comprise cooperating cam surfaces so that said twisting torque is converted to a removal force acting on said needle guard.

18. A method of providing a parenteral injection of liquid medicament, comprising:
   twisting an injection assembly with respect to a retraction assembly so that said injection assembly is simultaneously moved to an armed position and said retraction assembly is separated from a needle guard, said needle guard being engaged to a needle sheath so that separation of said needle guard from said retraction assembly removes said needle sheath from a hypodermic needle within said retraction assembly.

19. The method as in claim 18, further comprising activating said injection assembly so as to release an injection spring within said injection assembly so that said injection spring provides the parenteral injection through said hypodermic needle and energizes a retraction spring of said retraction assembly, wherein said retraction spring retracts said hypodermic needle into said retraction assembly after the parenteral injection.

20. The method as in claim 19, further comprising permanently resecuring said needle guard to said retraction assembly so that said needle sheath and said needle guard enclose said hypodermic needle within said retraction assembly.

* * * * *